(12) United States Patent
Cobabe

(10) Patent No.: US 10,821,027 B2
(45) Date of Patent: Nov. 3, 2020

(54) DEVICES FOR FILTERING SOUND AND RELATED METHODS

(71) Applicant: Intermountain Intellectual Asset Management, LLC, Salt Lake City, UT (US)

(72) Inventor: Andrew L. Cobabe, River Heights, UT (US)

(73) Assignee: Intermountain Intellectual Asset Management, LLC, Salt Lake City, UT (US)

( * ) Notice: Subject to any disclaimer, the term of this patent is extended or adjusted under 35 U.S.C. 154(b) by 324 days.

(21) Appl. No.: 15/891,224

(22) Filed: Feb. 7, 2018

(65) Prior Publication Data
US 2018/0221207 A1 Aug. 9, 2018

Related U.S. Application Data

(60) Provisional application No. 62/456,172, filed on Feb. 8, 2017.

(51) Int. Cl.
*A61F 11/00* (2006.01)
*H04R 1/10* (2006.01)
*H04R 1/28* (2006.01)

(52) U.S. Cl.
CPC ............ *A61F 11/00* (2013.01); *H04R 1/1016* (2013.01); *H04R 1/2811* (2013.01)

(58) Field of Classification Search
CPC ...... A61F 11/00; H04R 1/1016; H04R 1/2811
USPC .......................................................... 181/135
See application file for complete search history.

(56) References Cited

U.S. PATENT DOCUMENTS

| 3,688,863 A * | 9/1972 | Johnson ................. H04R 25/48 |
| | | 181/135 |
| 4,222,393 A | 9/1980 | Hocks et al. |
| 4,680,798 A | 7/1987 | Neumann |
| 4,852,683 A | 8/1989 | Killion |

(Continued)

FOREIGN PATENT DOCUMENTS

WO 2008087157 7/2008

OTHER PUBLICATIONS

Lugli, et al., The Windowed Sound Therapy: A New Empiracal Approach for an Effective Personalized Treatement of Tinnitus, International Tinnitus Journal, vol. 15, No. 1, 51-61 (2009).

*Primary Examiner* — Forrest M Phillips
(74) *Attorney, Agent, or Firm* — Stoel Rives LLP; Jordan B. Olsen

(57) ABSTRACT

A sound-filtering device can include an entry port that receives sound from an environment when the device is coupled to an ear of a user. The device can further include an exit port that delivers sound that has passed through the device to the ear of the user. The device can further include a channel extending between the entry port and the exit port to define a path along which sound travels from the entry port to the exit port. The device can also include a side port in fluid communication with the channel and a resonant chamber offset from the path defined by the channel and in fluid communication with the channel via the side port. The resonant chamber can attenuate at least a portion of any sound passing through the channel that is within a band of frequencies narrower than a full audible spectrum of the user.

20 Claims, 28 Drawing Sheets

(56) References Cited

U.S. PATENT DOCUMENTS

| | | | |
|---|---|---|---|
| 5,024,612 A * | 6/1991 | van den Honert | A61F 11/00 604/36 |
| 5,113,967 A | 5/1992 | Killion et al. | |
| 5,167,236 A | 12/1992 | Junker | |
| 5,303,306 A | 4/1994 | Brillhart et al. | |
| 5,325,872 A | 7/1994 | Westermann | |
| 5,332,871 A * | 7/1994 | Carrigan | A61F 11/08 181/135 |
| 5,403,262 A | 4/1995 | Gooch | |
| 5,735,885 A | 4/1998 | Howard et al. | |
| 5,788,656 A | 8/1998 | Mino | |
| 5,795,287 A | 8/1998 | Ball et al. | |
| 5,930,371 A * | 7/1999 | Cheng | F01N 1/023 381/71.5 |
| 5,933,801 A | 8/1999 | Fink et al. | |
| 5,936,208 A * | 8/1999 | Hamery | A61F 11/08 181/135 |
| 6,041,129 A | 3/2000 | Adelman | |
| 6,047,074 A | 4/2000 | Zoels | |
| 6,048,305 A | 4/2000 | Bauman et al. | |
| 6,115,478 A | 9/2000 | Schneider | |
| 6,201,875 B1 | 3/2001 | Davis et al. | |
| 6,394,969 B1 | 5/2002 | Lenhardt | |
| 6,606,391 B2 | 8/2003 | Brennan et al. | |
| 6,610,019 B2 | 8/2003 | Choy | |
| 6,846,284 B2 | 1/2005 | Choy | |
| 6,974,410 B2 | 12/2005 | Micheyl et al. | |
| 7,081,085 B2 | 7/2006 | Viirre et al. | |
| 7,347,827 B2 | 3/2008 | Choy | |
| 7,520,851 B2 | 4/2009 | Davis et al. | |
| 7,613,519 B2 | 11/2009 | Ridder | |
| 7,720,245 B2 | 5/2010 | Bauman et al. | |
| 7,751,580 B2 | 7/2010 | Bauman | |
| 8,043,203 B2 | 10/2011 | Park et al. | |
| 8,054,985 B2 | 11/2011 | Doty | |
| 8,088,077 B2 | 1/2012 | Turner et al. | |
| 8,249,285 B2 | 8/2012 | Killion et al. | |
| 8,273,034 B2 | 9/2012 | Fogel et al. | |
| 8,306,248 B2 | 11/2012 | Digiovanni et al. | |
| 8,353,846 B2 | 1/2013 | Henry et al. | |
| 8,567,555 B2 * | 10/2013 | Harvey | H04R 1/1016 181/129 |
| 8,579,796 B2 | 11/2013 | Winkler | |
| 8,608,638 B2 | 12/2013 | McGuire | |
| 8,666,099 B2 | 3/2014 | Nielsen | |
| 8,820,470 B2 * | 9/2014 | Brown | A61F 11/08 128/864 |
| 8,888,712 B2 | 11/2014 | Turner et al. | |
| 8,917,890 B2 | 12/2014 | Digiovanni et al. | |
| 9,242,067 B2 | 1/2016 | Shore et al. | |
| 9,282,917 B2 | 3/2016 | Drexler et al. | |
| 2003/0114728 A1 | 6/2003 | Choy | |
| 2005/0194207 A1 * | 9/2005 | Nemit, Jr. | F02M 35/1222 181/250 |
| 2006/0042868 A1 * | 3/2006 | Berg | A61F 11/10 181/135 |
| 2007/0230713 A1 | 10/2007 | Davis | |
| 2009/0307590 A1 | 12/2009 | Frater et al. | |
| 2010/0121411 A1 | 5/2010 | Hochmair et al. | |
| 2012/0046713 A1 | 2/2012 | Hannemann et al. | |
| 2012/0203301 A1 | 8/2012 | Cameron et al. | |
| 2012/0283593 A1 | 11/2012 | Searchfield et al. | |
| 2013/0039517 A1 | 2/2013 | Nielsen et al. | |
| 2013/0204170 A1 | 8/2013 | Zeng et al. | |
| 2013/0343581 A1 | 12/2013 | Drylund | |
| 2014/0356824 A1 | 12/2014 | Dozier | |
| 2014/0363007 A1 | 12/2014 | Digiovanni et al. | |
| 2015/0256948 A1 | 9/2015 | Nielsen | |

* cited by examiner

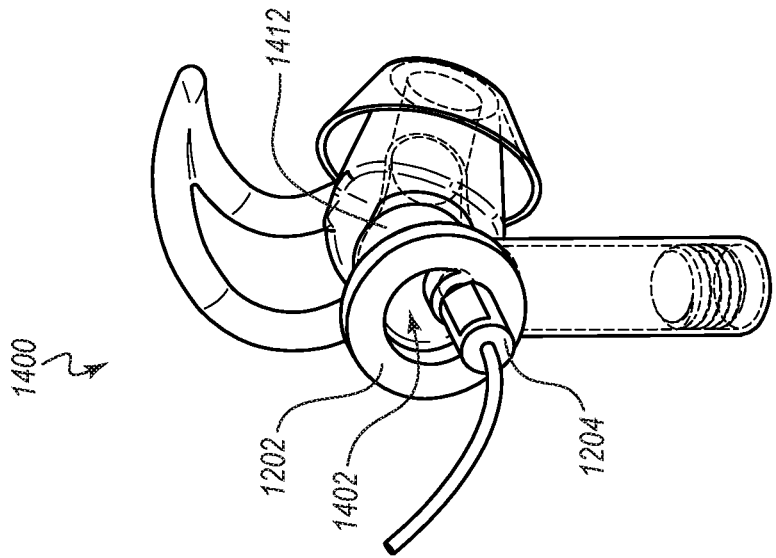
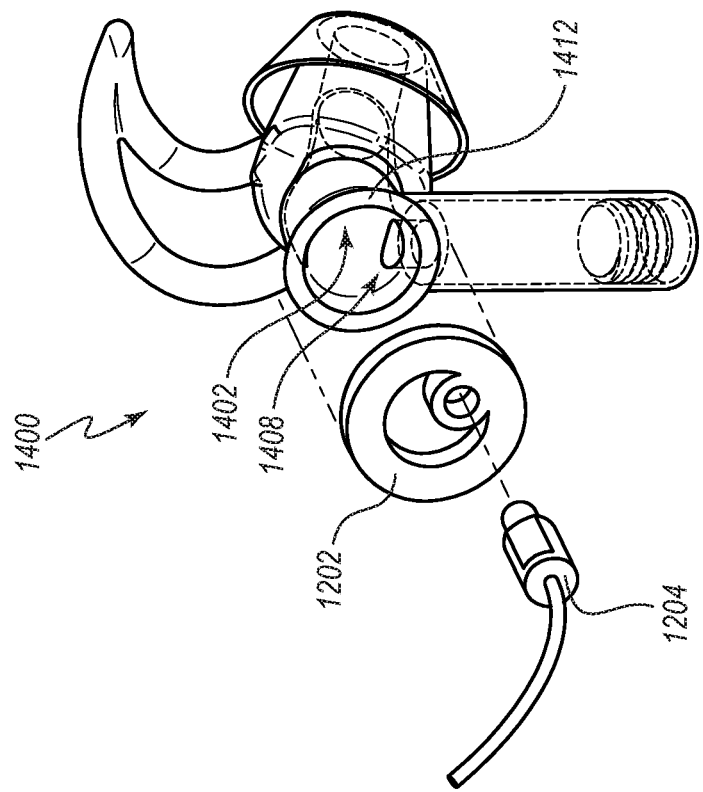
FIG. 27B
FIG. 27A

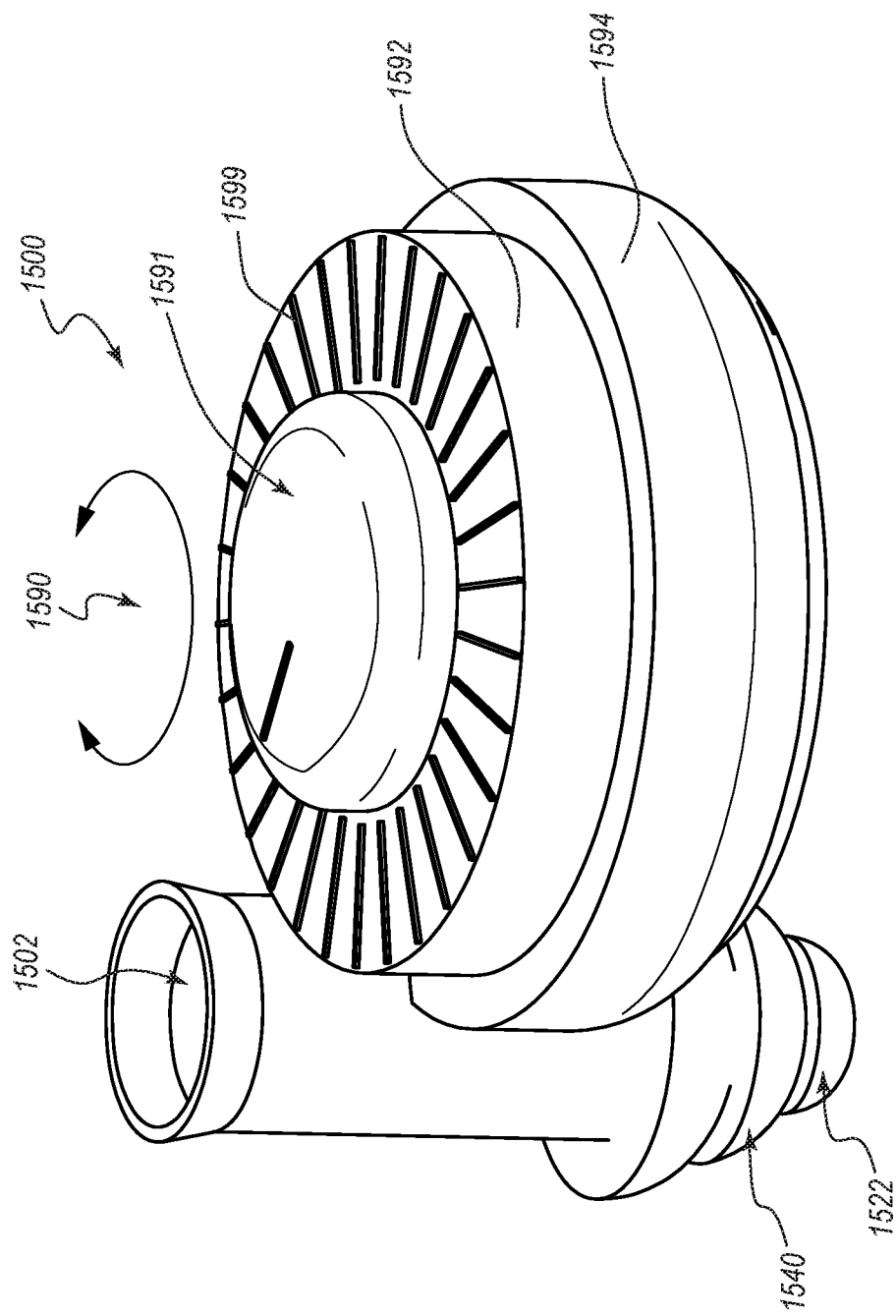

DEVICES FOR FILTERING SOUND AND RELATED METHODS

RELATED APPLICATIONS

This application claims priority to U.S. Provisional Application No. 62/456,172, filed on Feb. 8, 2017 and titled "Devices for Filtering Sound and Related Methods," which is incorporated herein by reference in its entirety.

BACKGROUND

The present disclosure relates to devices for filtering sound. In particular, the present disclosure relates to wearable devices for notch filtering sound.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 27A is a perspective view of another embodiment of a sound-filtering device;

FIG. 27B is another perspective view of the sound-filtering device of FIG. 27A;

FIG. 28 is a perspective view of another embodiment of a sound-filtering device;

DETAILED DESCRIPTION

Figure 1:
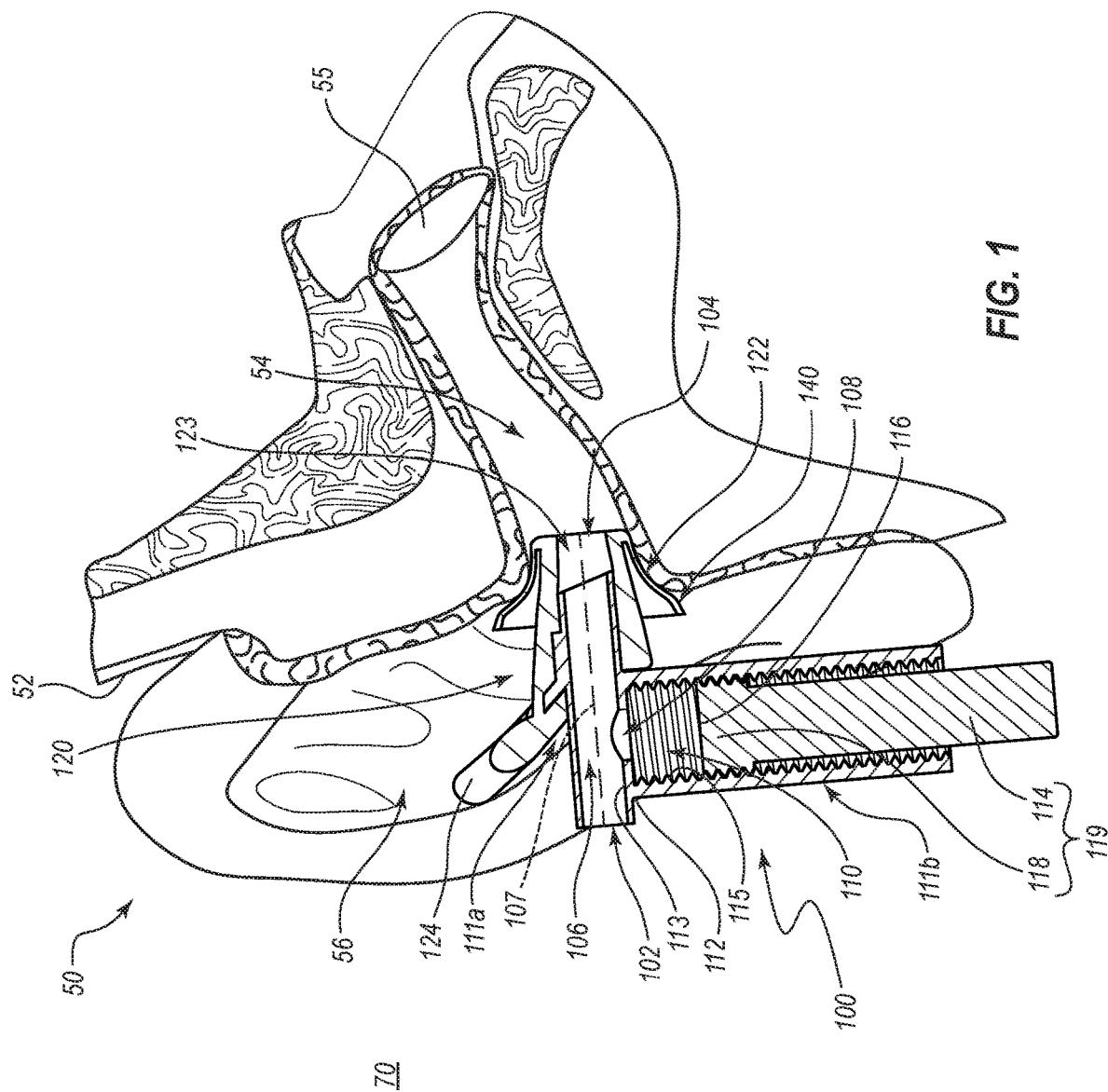
FIG. 1 is a cross-sectional view of an embodiment of a sound-filtering device coupled with the right ear of a user.

Various epidemiological surveys indicate that 5-15% of the population have tinnitus. The U.S. Centers for Disease Control estimates that over 50 million Americans have some form of tinnitus, with roughly 20 million of these struggling with burdensome forms and roughly 2 million suffering from debilitating cases. (2011-2012 National health and Nutrition Examination Survey conducted by the U.S. Centers for Disease Control.) In one form of tinnitus, known as tonal tinnitus, the individual perceives nearly continuous sound at a well-defined frequency. For example, an individual may perceive a tone at a frequency of around 4,000 Hz, 7,500 Hz, or some other value. In further instances, the individual may simultaneously perceive sounds at multiple distinct tones, which may be referred to as multi-tonal tinnitus. In other forms of tinnitus, the individual perceives noise-like sounds.

Studies have shown that tinnitus may be treated by providing patients with auditory stimulation consisting of broadband sound and/or noise that contains a notch (e.g., a silent window) centered at the tinnitus frequency. For example, in one study, the auditory stimulation consisted of a recording of white noise from which a window of frequencies centered at the patient's tinnitus frequency had been removed. (Marco Lugli et al., "The Windowed Sound Therapy: A New Empirical Approach for an Effective Personalized Treatment of Tinnitus," International Tinnitus Journal, Vol. 15, No. 1, 51-61 (2009).) The patients listened to the recording continually for 1.5-3 hours per day for a period of 2 to 12 months. This treatment yielded a significant long-term reduction of tinnitus loudness, annoyance, and/or distress. It was observed that the notched stimulus induced neuroplastic changes to auditory cortex activity and inhibitory networks associated with tinnitus.

Certain embodiments disclosed herein can provide new approaches for treating tinnitus. Some embodiments can also provide new approaches for altering an acoustic stimulus and/or modifying a sound to bring about changes in tinnitus perception. Certain embodiments comprise wearable sound-filtering devices. A device can include a channel that passes sound to the user with little or no alteration at most frequencies. The device can include a resonant chamber that attenuates a portion of the sound that falls within a band of frequencies, which may be centered on a target frequency. Accordingly, the device can operate as a notch filter, and the notch can be centered on the target frequency. Certain embodiments can be adjustable, such that a user may tune the device to select the target frequency that the device attenuates. The sound-filtering device can be worn continuously, the user may wear the device according to desire or preference, and/or the user may wear the device for specific periods designated by a treatment regimen. By operating as a notch filter, the device may be used for instantaneous relief from the symptoms of tinnitus and/or for treating tinnitus so as to fundamentally improve the condition. One or more of these and/or other uses and/or advantages of devices disclosed herein will be apparent from the present disclosure.

Moreover, although much of the discussion herein is presented in the context of treating or otherwise alleviating the symptoms of tinnitus, the present disclosure is not limited to this context. Indeed, various embodiments can desirably be used in other or further settings. For example, filtering of sound to attenuate a portion of the sound that falls within a band of frequencies (e.g., a narrow band of frequencies), while permitting the remainder of the sound to proceed to the ear in unaltered or slightly altered form, can be desirable in contexts involving machine operation, such as in manufacturing, construction, landscaping, dentistry, or other sectors. For example, where a machine (e.g., lawnmower, leaf blower, etc.) or other device produces noise only or predominantly at one or more characteristic frequencies, embodiments of devices disclosed herein may be used to attenuate one or more of these characteristic frequencies, while permitting the individual wearing the device to hear other sounds with little to no attenuation. Numerous other applications are also contemplated. For example, embodiments may be used to eliminate feedback in hearing aids. These and other applications will be apparent from the present disclosure.

FIG. 1 depicts an embodiment of a sound-filtering device 100 coupled with an ear 50 (or a portion of an ear 50) of a user 52. In particular, the device 100 is coupled with the right ear 50 (or a portion of the right ear 50) of the user 52, which includes an ear canal 54 leading to an eardrum 55 and an exposed pinna 56. The device 100 includes an entry port 102 that is exposed to an environment 70 that surrounds the user 52. During use, sound from the environment 70 can be received through the entry port 102. The device 100 further includes an exit port 104 that delivers sound that has passed through the device 100 to the ear 50. In particular, in the illustrated arrangement, the exit port 104 is positioned within and is in fluid communication with the ear canal 54. Accordingly, sound that exits the device 100 via the exit port 104 travels through the ear canal 54 to the eardrum 55. The term "fluid communication" is used in a broad sense and includes arrangements in which a fluid (e.g., air) is capable of being conducted or otherwise passing from one entity to another.

The device 100 further includes a channel 106 that extends between the entry port 102 and the exit port 104. The channel 106 defines a path 107 along which sound travels from the entry port 102 to the exit port 104. In the illustrated embodiment, the path 107 is substantially rectilinear. In FIG. 1, the path 107 is represented by a single line for purposes of illustration. In other embodiments, the path 107 can be curved or can define any other suitable shape along which sound can be conducted from the entry port 102 to the exit port 104. For example, in stating that the channel 106 and the path 107 defined thereby extend between the entry port 102 and the exit port 104, there is no implication that every portion of the channel 106 and the path 107 must be physically between (i.e., be intersected by a straight line that extends between) the ports 102, 104. In some embodiments, the channel 106 and the path 107 may deviate significantly from a straight line extending between the ports 102, 104. The path 107 can correspond to a full or partial volume of the channel 106, depending on the manner in which sound propagates through the channel 106.

Figure 3:
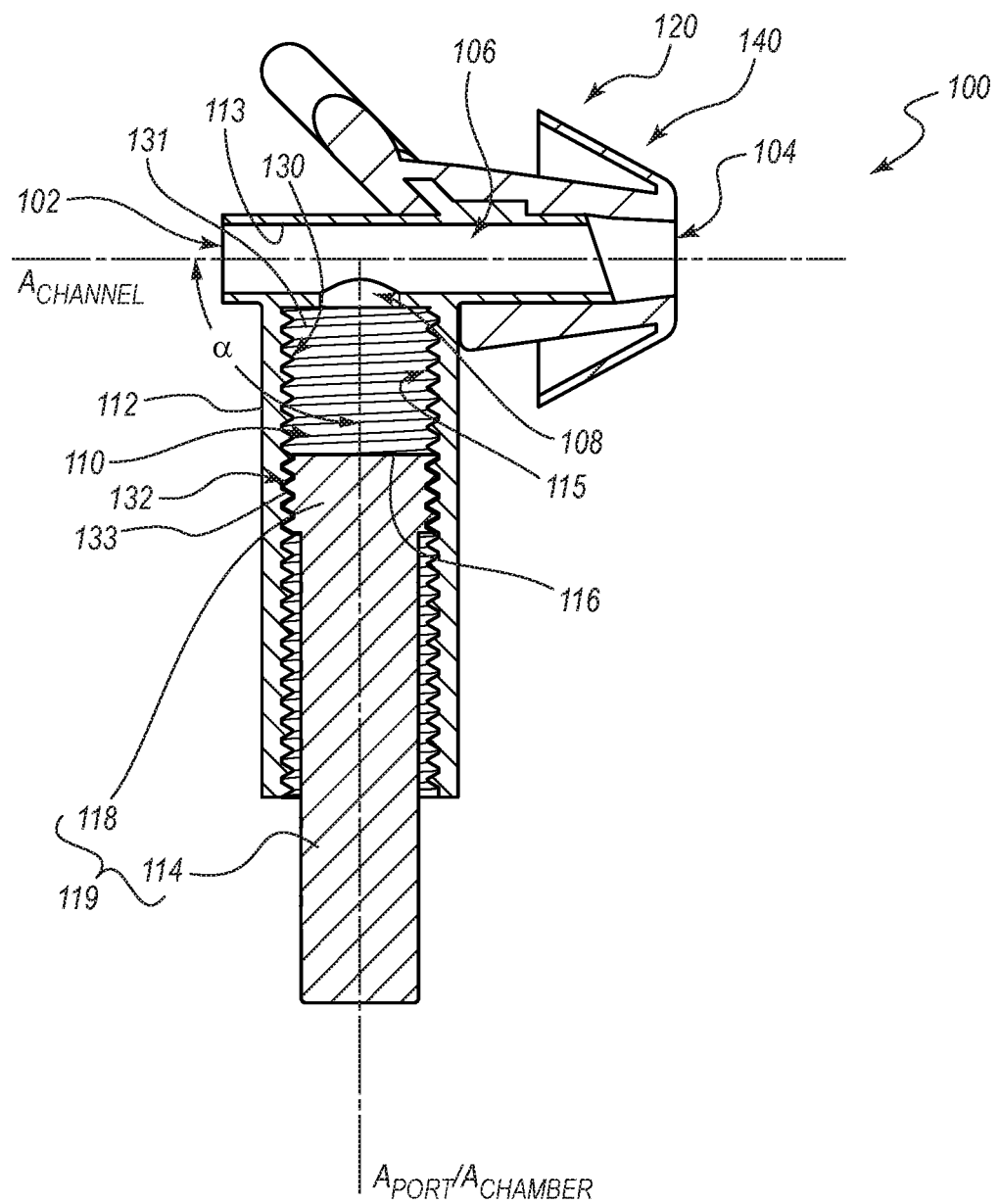
FIG. 3 is another cross-sectional view of the sound-filtering device of FIG. 1 taken along the view line 3-3 in FIG. 2, the sound-filtering device including a resonant chamber in a first volumetric state.
Figure 4:
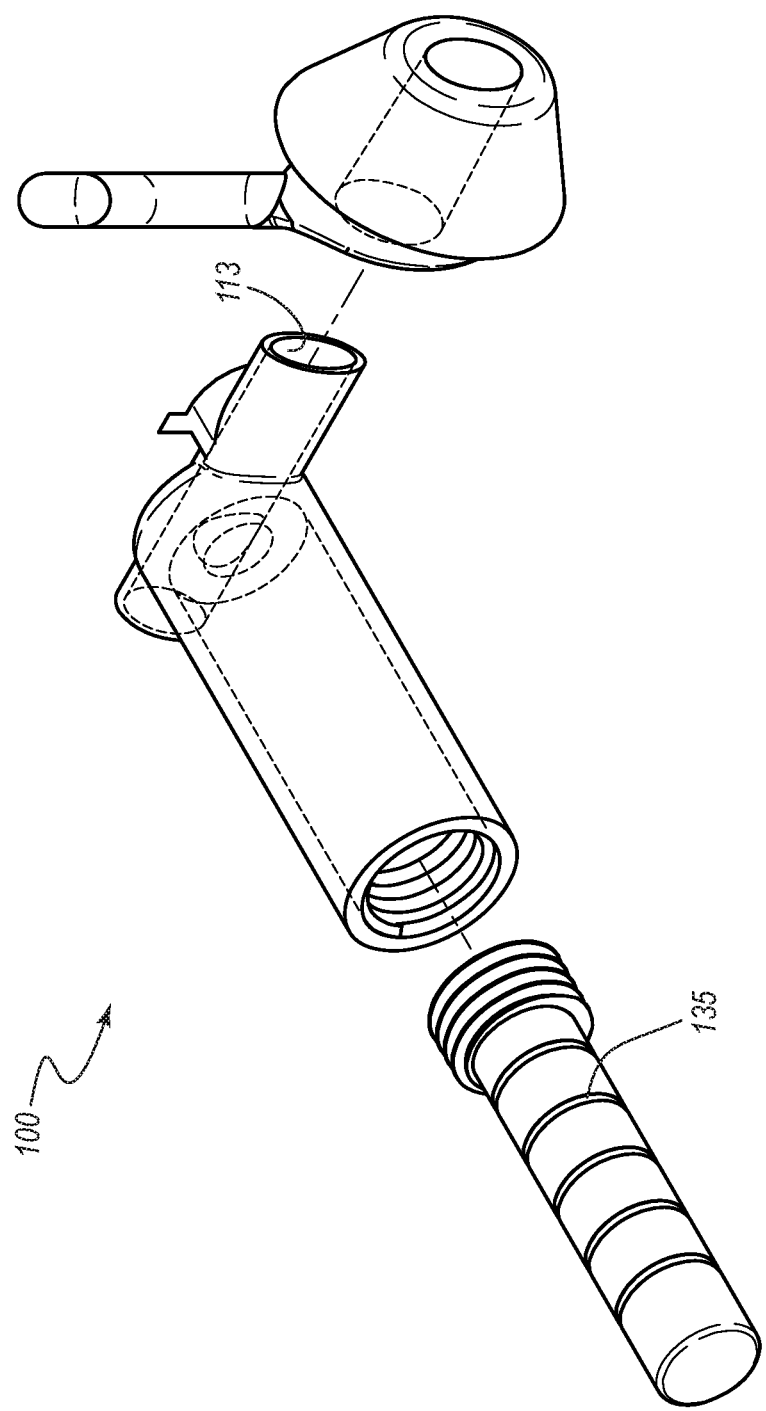
FIG. 4 is an exploded perspective view of the sound-filtering device of FIG. 1.

In the illustrated embodiment, the channel 106 is defined by a first branch 111a of a housing element 112 and an insert portion 122 of an anchor system 120. With reference to FIGS. 1, 3, and 4, the first branch 111a of the housing element 112 includes a sidewall 113 that defines a proximal portion of the channel 106. In the illustrated embodiment, the sidewall 113 is shaped substantially as an elliptical cylinder. A proximal end of the sidewall 113 defines the entry port 102. A distal end of the sidewall 113 is encompassed by the insert 122 of the anchor system 120. With further reference to FIG. 1, a lumen 123 that extends through the insert 122 defines the distal end of the channel 106. The distal end of the channel portion of the housing element 112 can be secured to the anchor system 120 in any suitable manner.

In some embodiments, a cross-sectional area of the channel 106 in a direction transverse to a direction of sound travel through the channel 106 either does not decrease or decreases by only a small amount between the entry port 102 and the exit port 104. Stated otherwise, a transverse cross-sectional area of the channel 106 can be substantially constant along a full length of the channel 106. In various embodiments, the transverse cross-sectional area of the channel 106 decreases by no more than 15, 20, or 25 percent between the entry and exit ports 102, 104.

In some embodiments, it can be desirable for the channel 106 to permit sound to flow through it in a substantially uninhibited way. For example, in some instances, a user 52 may wish to hear sounds from the environment 70 that do not fall within an attenuation range of frequencies as clearly as possible. In some instances, the channel 106 may have a relatively large transverse cross-section, and may define a cross-sectional area that is no less than 50, 60, or 70 percent of a cross-sectional area of the ear canal 54 at the position of the exit port 104.

In some embodiments, a minimum cross-sectional area of the channel 106 in a direction transverse to a direction of travel of sound through the channel 106 is no less than one third or one half of an area defined by an outer perimeter of the device at a longitudinal position of the exit port 104. In the illustrated embodiment, this outer perimeter is defined by the distal tip of the insert 122—that is, an outer surface of the distal tip of the insert 122 defines the outer perimeter, and an inner surface of the distal tip of the insert 122 defines an opening of the exit port 104.

In various embodiments, the channel 106 is free of obstructions. Stated otherwise, the channel 106 can be fully open. The channel 106 may be devoid of physical sound-dampening components, such as filters, plugs, etc. In other embodiments, the channel 106 may comprise a filter. For example, a filter may be used to reduce certain resonant peaks that may be caused by the shape, size, and/or length of the channel 106 or device 100. These resonant peaks can differ from those attributed to the resonant chamber 110.

With continued reference to FIG. 1, the device 100 can include a side port 108 that is in fluid communication with the channel 106. The device 100 can further include a resonant chamber 110, which may also be referred to as a resonant cavity 110, that is offset from the path 107 defined by the channel 106. Stated otherwise, the path 107 does not pass through the resonant chamber 110, or the resonant chamber 110 is spaced apart from or is adjacent to the path 107. Stated in yet another manner, sound is capable of passing through the channel 106 along the path 107 without passing through the resonant chamber 110.

The resonant chamber 110 is configured to attenuate specific or targeted portions of sound that pass through the channel 106. For example, without being limited by theory, one physical phenomenon that can lead to attenuation of specific frequencies is energy dissipation. When the sound that passes through the channel 106 includes a frequency (or frequencies) that corresponds to the natural resonance of the resonant chamber 110 (e.g., a resonance due to air within the resonant chamber 110 and/or interactions of the air with the walls that define the resonant chamber 110), energy from that frequency (or those frequencies) of sound is used to set up or maintain this natural resonance. As a result, this frequency is (or frequencies are) attenuated and is (or are) thus present to a lesser degree in the sound that passes through the exit port 104 and is ultimately delivered to the eardrum 55.

The resonant chamber 110 may have a single resonant frequency. For example, the resonant chamber 110 may operate as a Helmholtz resonator. In practice, a resonant chamber 110 may attenuate not only the resonant frequency, but also frequencies that neighbor the resonant frequency. The narrowness of the band of frequencies that are attenuated by the device 100 can depend on a Q factor of the device 100 or the resonant chamber 110. Stated otherwise, the Q factor can correspond to how well the resonant chamber 110 targets a frequency. Higher Q factors can correspond to narrower bands of frequencies that are attenuated. In some instances, rigid materials can yield higher Q factors. For example, a device 100 that includes a rigid polycarbonate might attenuate a narrower band of frequencies than a like-constructed device that includes silicone in place of the polycarbonate.

The resonant chamber 110 may be said to attenuate at least a portion of any sound that passes through the channel 106 that is within an attenuation band of frequencies. For example, if the sound that passes through the channel 106 is at frequencies that are entirely within the band of frequencies that the resonant chamber 110 attenuates, then all of the sound passing through the channel 106 may be attenuated. Some frequencies may be attenuated more than others—for example, a portion of the sound at the resonant frequency of the resonant chamber 110 may be attenuated more than any other portion of the sound—but each frequency of sound may undergo at least some attenuation. In other instances, the sound that passes through the channel 106 may be at frequencies that are both within and without the attenuation band. Sound that is outside the attenuation band may be substantially unaltered or unaffected by the resonant chamber 110. In still further instances, sound that passes through the channel may be at frequencies that are exclusively outside of the attenuation band, and these may likewise be substantially unaltered or unaffected by the resonant chamber 110.

In certain embodiments, the device 100 can also be configured to amplify frequencies that are near or adjacent to the frequency band that is being attenuated. For example, the device 100 can be configured to amplify sound that is at a frequency adjacent the upper and/or lower end of the attenuation band.

In many embodiments, the attenuation band of frequencies can be smaller than a full audible spectrum of the user. A typical hearing range for a healthy young human is from 20 Hz to 20 kHz. However, this hearing range can differ due to such factors as age or anatomy. For example, a middle-aged adult human may have a hearing range that tops out at 14 kHz. Regardless of the specific hearing range of a given user, embodiments of the device can be capable of attenuating sounds that fall within a range that is far smaller than the full hearing range of the user. For example, in various embodiments, the device 100 can attenuate sounds within a band of frequencies that spans no more than 2 octaves, 1.5 octaves, or 1 octave. In some instances, the device 100 can attenuate sounds within a band of frequencies that spans about one octave.

Figure 24:
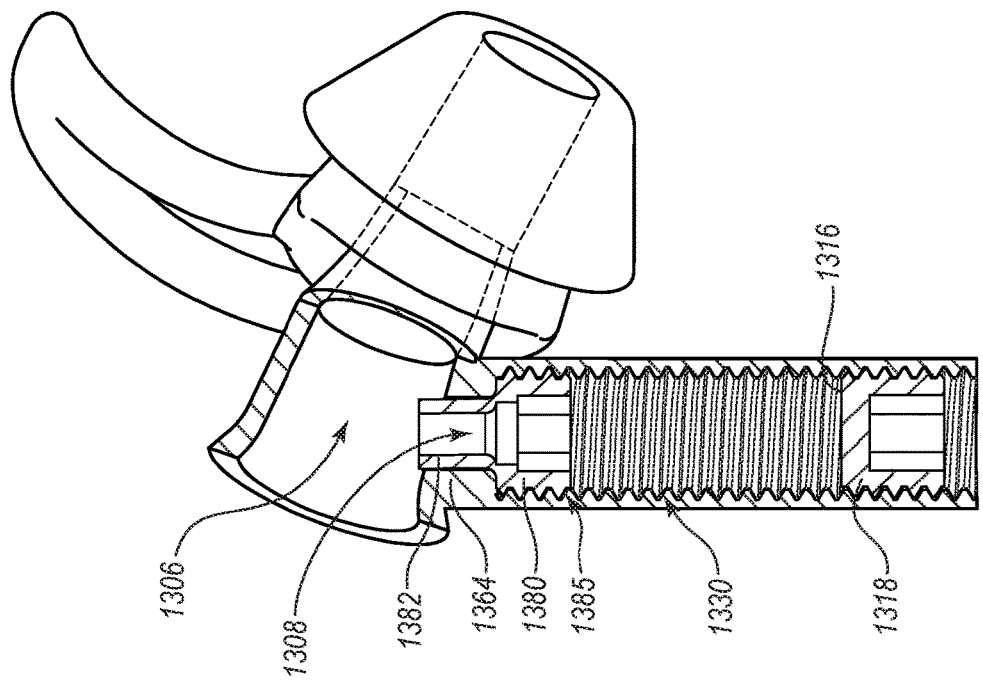
FIG. 24 is a cross-sectional view of the sound-filtering device of FIG. 21 that includes an adjustable nozzle.
Figure 23:
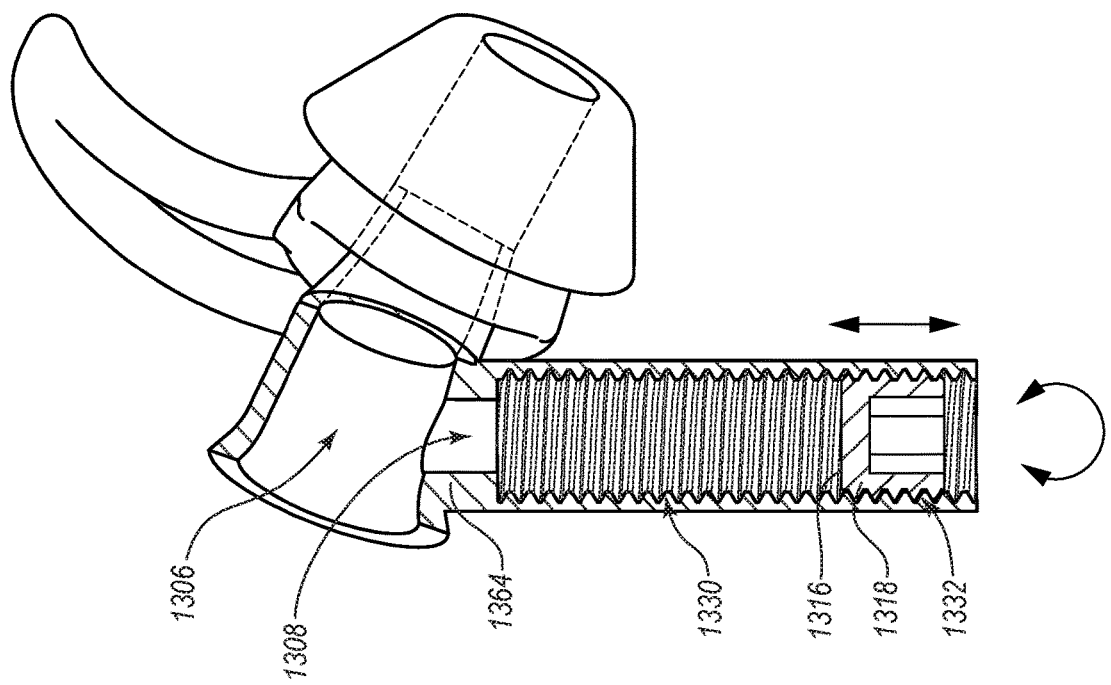
FIG. 23 is a cross-sectional view of the sound-filtering device of FIG. 21.

In certain embodiments, the features and/or components of the device 100 can be adjusted and/or selected to notch or otherwise attenuate sounds at any desired frequency across the range of human hearing. For example, the resonant chamber 110 can be made larger or smaller to attenuate a desired frequency. The size of the port 108 can also be changed to affect the resonant frequency. In other embodiments, an adjustment nozzle can be added at or adjacent the port 108 to affect the resonant frequency (as shown in FIG. 24). Other features and/or components can also be adjusted and/or selected as desired.

Figure 5:
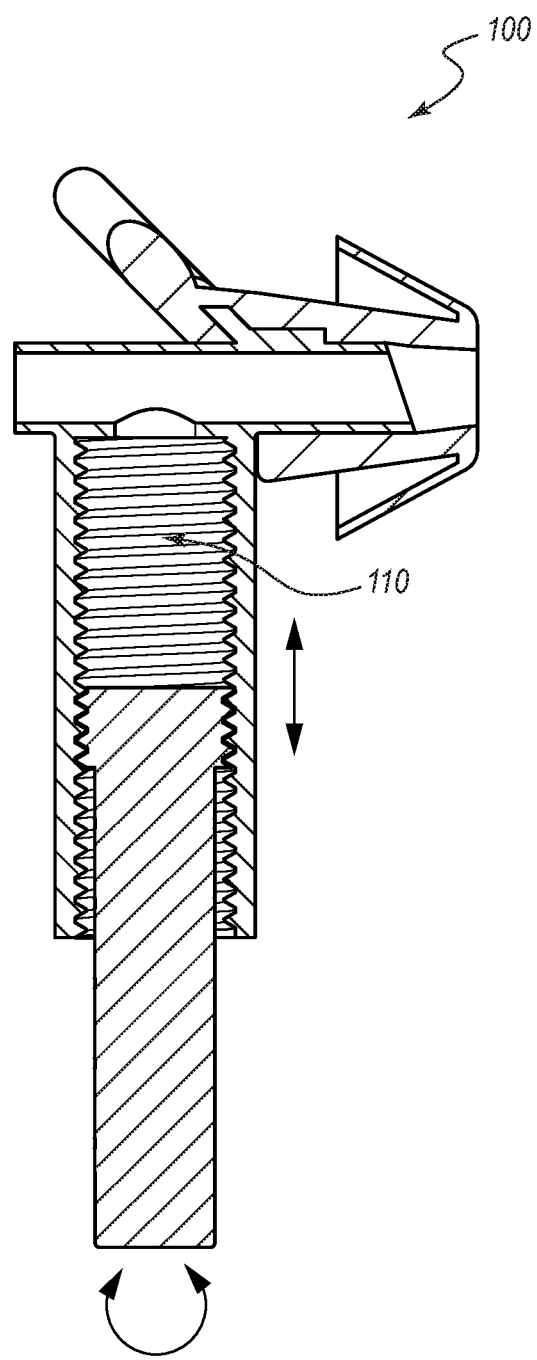
FIG. 5 is another cross-sectional view of the sound-filtering device of FIG. 1 such as the view depicted in FIG. 3, the resonant chamber of the sound-filtering device being in a second volumetric state in which a geometric volume of the resonant chamber is larger than the geometric volume of the resonant chamber when in the first volumetric state depicted in FIG. 3.

With reference to FIGS. 1, 3, and 5, in certain embodiments, a geometric volume of the resonant chamber 110 can be selectively adjustable. For example, a user 52 may be able to tune the device 100 to a target frequency that corresponds with the frequency at which the user 52 experiences tinnitus.

In the illustrated embodiment, the housing element 112 of the device 100 includes a second branch 111b that defines a portion of the resonant chamber 110. In particular, a sidewall 115 of the second branch 111b defines a sidewall of the resonant chamber 110. In the illustrated embodiment, the sidewall 115 is substantially cylindrical. The sidewall 115 can also be circular or any other shape, including shapes that follow the contour of the ear, if desired. The device 100 further includes a post 114 coupled to a piston 118 or cap that closes a proximal end of the second branch 111b. In particular, the piston 118 defines an end wall 116 that defines a proximal end of the resonant chamber 110. In the illustrated embodiment, the piston 118 and the post 114 are integrally formed of a unitary piece of material, although other arrangements are contemplated. The end wall 116 can be moved relative to the housing element 112 to adjust the geometric volume of the resonant chamber 110. Together, the post 114 and the piston 118 may be referred to as a frequency adjustment member 119.

With reference to FIGS. 3 and 5, the housing element 112 can define an internal adjustment interface 130 and the end wall 116 can define an external adjustment interface 132 that cooperates with the internal adjustment interface 130 to effect adjustment of the geometric volume of the resonant chamber 110. Any suitable adjustment interfaces 130, 132 are contemplated. For example, in some embodiments, a detent system may be used to transition the resonant chamber 110 between discrete volumetric states. In the illustrated embodiment, the adjustment interfaces are internal 130, 131 and external threading 132, 133, that interact to permit continuous adjustment of the volume. In other or further embodiments, the post 114 may include external threading that interfaces with the internal threading 130.

In the illustrated embodiment, the post 114 extends proximally beyond a proximal end of the housing element 112 to permit manipulation of the end wall 116. Stated otherwise, a position of the end wall 116 can be adjusted by manipulating the post 114. As shown in FIG. 5, the post 114 can be rotated to adjust the longitudinal position of the end wall 116. In other embodiments, the post 114 may be manipulated in other manners, such as by pushing, pulling, screwing, and/or twisting. Other manners of adjustment are also contemplated.

FIG. 3 depicts the device 100 in a first volumetric state, and FIG. 5 depicts the device 100 in a second volumetric state. Transitioning the device 100 between the first and second volumetric states can effect an alteration of the band of frequencies that is attenuated by the resonant chamber 110. For example, in the illustrated embodiment, transitioning the device 100 from the first volumetric state (FIG. 3) to the second volumetric state (FIG. 5) can shift the band of frequencies downward. That is, the band of frequencies can span a set of frequencies that has a higher value when the device 100 is in the first volumetric state, as compared with the set of frequencies spanned by the band of frequencies when the device 100 is in the second volumetric state. Similarly, in the illustrated embodiment, transitioning the device 100 from the second volumetric state (FIG. 5) to the first volumetric state (FIG. 3) effects an opposite shifting of frequencies.

Figure 2:
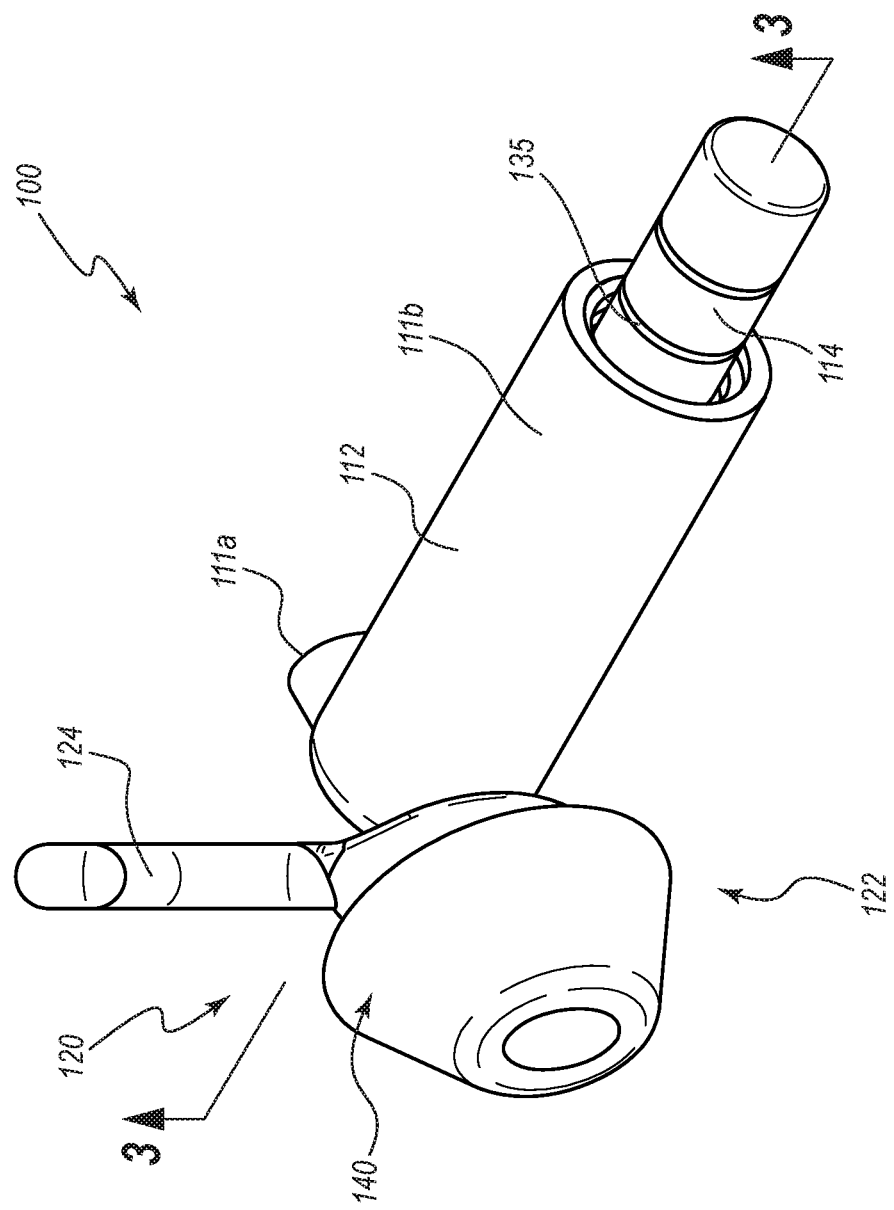
FIG. 2 is a perspective view of the sound-filtering device of FIG. 1 shown decoupled from the ear of the user.

With reference to FIGS. 2 and 4, the device 100 can include a plurality of markings 135. Each marking 135 can correspond to a frequency at which maximum attenuation is achieved via the resonant chamber 110. For example, the marking 135 can represent the resonant frequency of the resonant chamber 110. In the illustrated embodiment, each marking 135 includes a horizontal line (e.g., a printed line, a groove, etc.). The line of a particular marking 135 can be aligned with a proximal end of the second branch 111b of the housing element 112 to achieve a predetermined volumetric state of the resonant chamber 110. The marking 135 can additionally include any suitable indicia (not shown) to indicate information associated with the corresponding volumetric state of the device 100. For example, a marking 135 can include printing that indicates the target frequency (or resonant frequency, or frequency of maximum attenuation) that is most effectively attenuated when the device 100 is in the volumetric state associated with the marking 135. By way of example, a particular marking 135 may include both a horizontal line and the printed indicia "4,000 Hz." When this marking 135 is aligned with the proximal end of the branch 111b, the device 100 can be configured to attenuate a band of frequencies that includes (e.g., is centered or substantially centered on) 4,000 Hz, and may achieve maximum attenuation of 4,000 Hz sounds that pass through the device 100. The remaining markings 135 may include similar information corresponding to other volumetric states and other target frequencies. In other embodiments, markings 135 are not used, but a chart or graph can be used that associates the position of the frequency adjustment member 119 with a known attenuation or resonant frequency. For example, a chart or graph can be used that associates the number of turns of the frequency adjustment member 119 (from a flush or known starting position) with a known attenuation or resonant frequency (such as shown in the plot depicted in FIG. 30).

With reference to FIG. 3, the channel 106 can define a longitudinal axis $A_{CHANNEL}$ that extends in a direction of sound propagation through the channel 106. In the illustrated embodiment, the longitudinal axis $A_{CHANNEL}$ is substantially rectilinear. In other embodiments, the longitudinal axis $A_{CHANNEL}$ may be curved or otherwise configured to extend along a central line of a path through the channel 106. For example, if the channel 106 were instead somewhat S-shaped, the longitudinal axis $A_{CHANNEL}$ might likewise be S-shaped.

The side port 108 defines a central axis $A_{PORT}$ that extends through a center of a path through the side port 108. The central axis $A_{PORT}$ of the side port 108 can be positioned at a center of an opening defined by the housing element 112. In the illustrated embodiment, the side port 108 is defined by a short, substantially cylindrical sidewall formed as a bore through the housing element 112, and the central axis $A_{PORT}$ of the side port 108 corresponds to a central longitudinal axis through this opening. In various embodiments, the central axis $A_{PORT}$ of the side port 108 is at a nonzero angle α relative to the longitudinal axis $A_{CHANNEL}$ of the channel 106. In the illustrated embodiment, the angle α is 90 degrees. In other embodiments, the angle α is oblique. In some embodiments, the longitudinal axis $A_{CHANNEL}$ and the central axis $A_{PORT}$ intersect. In other embodiments, the longitudinal axis $A_{CHANNEL}$ and the central axis $A_{PORT}$ are nonintersecting.

The resonant chamber 110 can define a longitudinal axis $A_{CHAMBER}$. In the illustrated embodiment, the longitudinal axis $A_{CHAMBER}$ is collinear with the central axis $A_{PORT}$ of the side port 108. Other arrangements are also possible. For example, the longitudinal axis $A_{CHAMBER}$ and the central axis $A_{PORT}$ may be offset from each other at an angle and/or may be intersecting or nonintersecting. In various embodiments, the longitudinal axis $A_{CHAMBER}$ is at a nonzero angle α relative to the longitudinal axis $A_{CHANNEL}$ of the channel 106. In the illustrated embodiment, the angle α is 90 degrees. Indeed, in the illustrated embodiment, the housing element 112 that defines portions of the channel 106 and the resonant chamber 110 is substantially T-shaped. In other embodiments, the angle α is oblique. In some embodiments, the longitudinal axis $A_{CHANNEL}$ and the longitudinal axis $A_{CHAMBER}$ intersect. In other embodiments, the longitudinal axis $A_{CHANNEL}$ and the longitudinal axis $A_{CHAMBER}$ are nonintersecting (see FIG. 16).

With reference again to FIG. 1, the anchor system 120 can be configured to secure the device 100 to the ear 50 of the user 52. In some embodiments, the insert 122 is capable of securing the device 100 on its own. For example, in some embodiments, the insert 122 can be formed of a resiliently flexible material that may be deformed to a constricted state for insertion into the ear canal 54 and that may be permitted to return toward its natural state when within the ear canal 54. The insert 122 can provide sufficient force against an inner surface of the ear canal 54 to independently secure the device 100 to the ear 50 of the user 52. For example, in some embodiments, the insert 122 comprises a resilient foam.

In other or further embodiments, the insert 122 may be custom molded to the anatomy of the user 52. For example, an outer surface of the insert 122 may be custom shaped to fit snugly against an inner surface of the ear canal 54.

With reference to FIGS. 1-3, the insert 122 comprises a resilient member 140 configured to conform to a variety of different ear canal anatomies. In some embodiments, the resilient member 140 may independently provide sufficient force against the ear canal 54 to secure the device 100 to the ear 50. In other or further embodiments, the resilient member 140 may cooperate with an anchoring arm 124 to secure the device 100 to the ear 50. In some embodiments, the anchoring arm 124 comprises a resilient material that is configured to press against a suitable surface of the pinna 56 to secure the device 100 to the ear 50.

With continued reference to FIGS. 1-3, the resilient member 140 may be shaped substantially as a flexible cone, and may have an open proximal end and a closed distal end. As shown in FIG. 1, the open end faces outwardly toward the environment 70 and the closed end is positioned in the ear canal 54 when the device 100 is coupled to the ear 50. This arrangement can channel sound that would otherwise be admitted into the ear 50 toward the closed end. The closed end can inhibit this channeled sound from entering the ear canal 54. Stated otherwise, the insert 122 can reduce or eliminate sound that would otherwise enter the ear canal 54 along pathways around an exterior of the device 100.

In some embodiments, a universal flexible cone (e.g., a silicone dome) is used as the resilient member 140. Interchangeable resilient members (e.g., flexible cones) of various sizes and/or shapes can also be used. In further embodiments, the resilient member 140 comprises a custom molded shape that can be configured to fit with a portion of the user's ear.

In some embodiments, the anchor system 120 is selectively attachable to and detachable from the housing element 112. In other embodiments, the anchor system 120 may be permanently secured to or integrally formed with the housing element 112. In various embodiments, the anchor system 120 can comprise one or more resilient materials, such as silicone or foam. In other or further embodiments, the anchor system 120 can comprise one or more relatively rigid materials, such as molded plastic.

The housing element 112 can be formed of any suitable material. In some embodiments, one or more of the branches 111a, 111b of the housing element 112 may be relatively rigid. In various embodiments, one or more of the branches 111a, 111b of the housing element 112 comprise one or more of a plastic, elastomeric, or ceramic material. For example, in various embodiments, one or more of the branches 111a, 111b comprise one or more of a polycarbonate, polyethylene, polypropylene, polyvinylchloride, acrylonitrile butadiene styrene, acetyl, silicone, rubber, ethylene propylene rubber, nitrile, or ceramic nitride material. In the illustrated embodiment, the branches 111a, 111b are integrally formed of a unitary piece of material. In other embodiments, the branches 111a, 111b are formed of separate pieces that are joined together. In certain of such embodiments, the separate pieces may be selectively attachable to and detachable from each other. In other embodiments, the pieces may be permanently joined.

With reference to FIGS. 1-5, in some embodiments, the device 100 can be a purely mechanical device. For example, the device 100 may be devoid or free of electrical components. The device 100 may conveniently operate in the absence of a power source, such as a battery. The device 100 may also operate without any electrical analog-to-digital conversion, filtering, equalization, and/or other processing of sound. In some embodiments, the device 100 can be used in conjunction with one or more electrical devices. For example, in some embodiments, the device 100 may be coupled with a hearing aid, as further discussed below.

Figure 6:
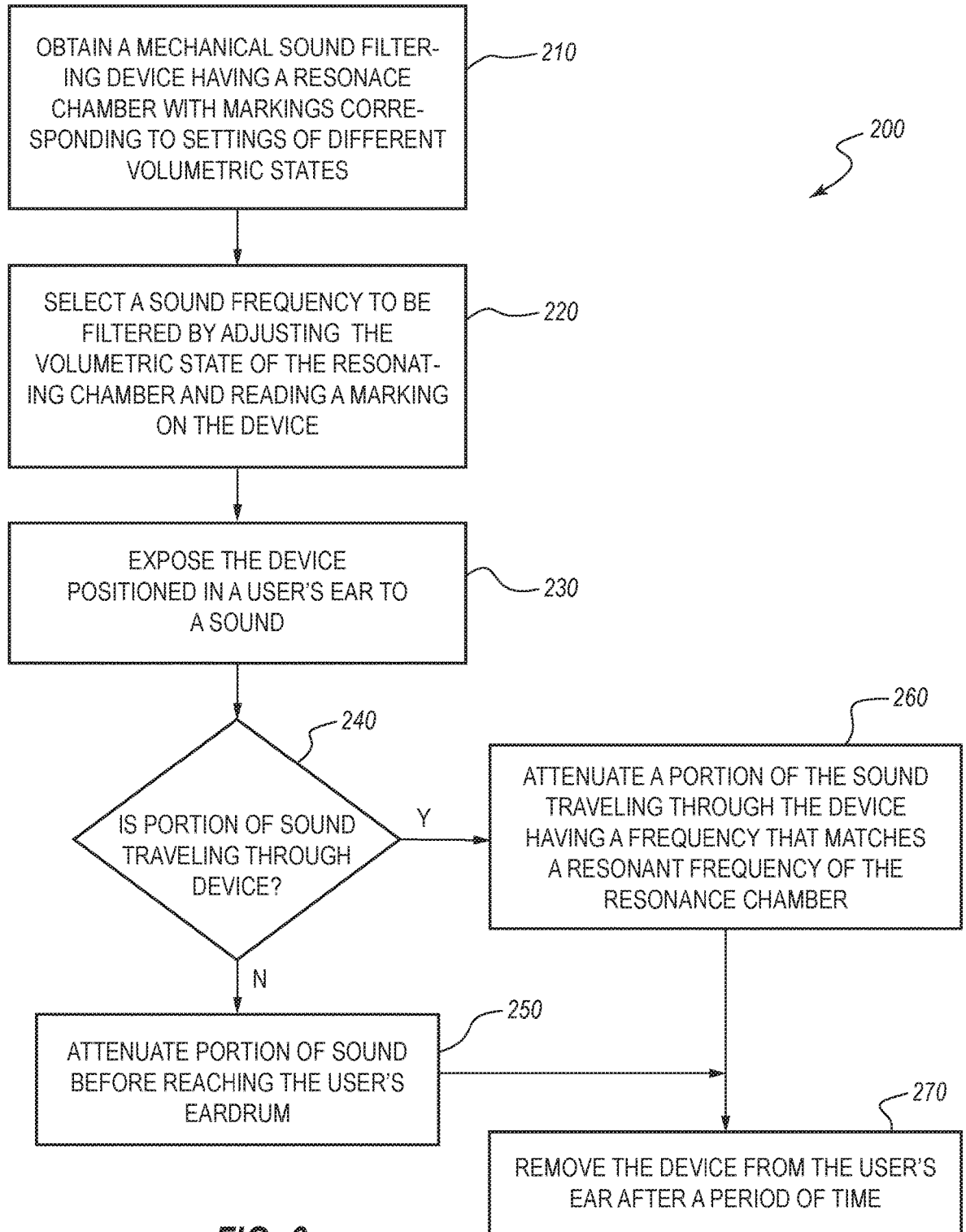
FIG. 6 is a flow diagram of an illustrative method of filtering sound using a sound-filtering device.

FIG. 6 is a flow diagram of an illustrative method 200 of filtering sound using a sound-filtering device, such as embodiments of the device 100 described above. In some instances, the method 200 begins at stage 210. At this stage, a mechanical sound-filtering device, such as the device 100, is obtained. For example, a user 52 may acquire the device 100 via any suitable mechanism, such as by purchase, removal from packaging, holding in a hand, etc. As with the embodiment illustrated in FIGS. 1-5, the device 100 may include a resonant chamber 110 that includes markings 135 that correspond to settings of different volumetric states of the resonant chamber 110. In other embodiments, the device 100 does not include markings 135.

At stage 220, a sound frequency that is to be filtered by the device 100 is selected on the device 100. In particular, the volumetric state of the resonant chamber 110 is adjusted. In some instances, this stage can include use of one or more of the markings 135 on the device 100. For example, a user might have tonal tinnitus at a specified frequency (e.g., 4,000 Hz). The user might obtain the knowledge of this frequency via any suitable method. Based on this knowledge, the user might then adjust a geometric volume of the resonant chamber 110 to ensure that the maximum sound attenuation occurs at 4,000 Hz. The user might adjust the geometric volume in any of the manners discussed above, such as by manipulating (e.g., rotating) the post 114, and can read one or more of the markings 135 to ensure that a volumetric state that corresponds to attenuation of 4,000 Hz sounds is achieved. For example, the user can ensure that a proximal end of the housing element 112 is aligned with one of the markings 135 that corresponds to 4,000 Hz. In other embodiments, the user may adjust the geometric volume of the resonant chamber 110 in accordance with a chart or graph that associates the position of the frequency adjustment member with the resonant frequency.

At stage 230, the device 100 is positioned in the user's ear 50 (or in a portion of the user's ear 50). While thus positioned, the device 100 is exposed to a sound in the environment 70.

Decision block 240 indicates that sound that comes into contact with the device 100 may follow a variety of different paths. If a portion of the sound passes around an exterior of the device 100 toward the ear canal 54, the method proceeds to stage 250. On the other hand, if a portion of the sound travels through the device 100—in particular, through the channel 106—the method proceeds to stage 260.

At stage 250, the portion of the sound the passes about the exterior of the device 100 is attenuated. For example, the cone-shaped resilient member 140 can attenuate the unfiltered sound in manners such as previously described. Ultimately, the method can pass from stage 250 to stage 270, which is described below.

At stage 260, a portion of the sound traveling through the device 100 having a frequency that matches a resonant frequency of the resonant chamber 110 is attenuated. For example, the user may attenuate a 4,000 Hz component of a sound as the sound passes through the device 100 via the mechanisms discussed above.

At stage 270, the device 100 is removed from the ear 50 after a period of time. The period of time may be selected by the user, for example, based on personal preference or based on a treatment regimen.

The illustrative method 200 can include more or fewer stages than those specifically noted in the flow chart of FIG. 6. Other flow charts depicting various methods for filtering sound are also contemplated, and can readily be constructed from the disclosures herein. For example, the discussions regarding operation of embodiments of the devices 100 and their components can readily be recited as methods. Further examples of methods are also now recited.

An illustrative method of modifying sound for delivery to an ear of a user can include a stage of obtaining a sound-filtering device, such as an embodiment of the device 100. The device 100 can include a resonant chamber 110 that defines a first geometric volume. The resonant chamber 110 can be configured to attenuate at least a portion of any sound passing through the device 100 that is within a first band of frequencies that is narrower than a full audible spectrum of the user when the resonant chamber 110 defines the first geometric volume.

The method can also include a stage of adjusting a size of the resonant chamber 110 such that the resonant chamber 110 defines a second geometric volume. The resonant chamber 110 can be configured to attenuate at least a portion of any sound passing through the device 100 that is within a second band of frequencies that is narrower than the full audible spectrum of the user when the resonant chamber 110 defines the second geometric volume. The second band of frequencies can be different from the first band of frequen-cies. The illustrative method can also include coupling the sound-filtering device 100 to the ear (or a portion of the ear) of the user.

In some instances, the sound-filtering device 100 comprises a plurality of markings 135, each marking corresponding to a different band of frequencies that can be attenuated by the device 100. Adjusting the size of the resonant chamber 110 can involve observing at least one of the plurality of markings 135 during the adjusting. In other embodiments, a graph, chart, or other form of instructions may be provided that associates the resonant frequency with the location of the frequency adjustment member 119. For example, a graph, chart, or other form of instructions may be provided that associates the number of turns of a frequency adjustment member 119 (from a flush or know starting position) with the resonant frequency.

In some instances, the sound-filtering device 100 comprises an end wall 116 that determines a volumetric state of the resonant chamber 110. Adjusting the size of the resonant chamber 110 can involve moving the end wall 116 to achieve the second geometric volume. In some instances, adjusting the size of the resonant chamber 110 comprises aligning the end wall 116 with one of the plurality of markings 135.

In some instances, adjusting the size of the resonant chamber 110 takes place after the sound-filtering device 100 is obtained. For example, a user may obtain the device 100, such as by purchasing the device 100, removing the device 100 from packaging, or holding the device 100 in a hand. Thereafter, the user may adjust the size of the resonant chamber 110.

Other or further methods can include one or more of the following stages: attenuating at least a portion of sound passing through the device via the resonant chamber after said coupling of the sound-filtering device to a portion of the ear of the user; or decoupling the sound-filtering device from the ear of the user after a period of use. Some methods include a stage of admitting sound into the sound-filtering device, attenuating at least a portion of the sound that is within the second band of frequencies to yield an altered sound, and delivering the altered sound to the ear of the user. In certain of such methods, said admitting, attenuating, and delivering are achieved without any electronic processing of either the sound or the altered sound. In other or further methods, said delivering involves directly delivering the altered sound to the ear of the user.

An illustrative method of treating tinnitus can include a stage of coupling a sound-filtering device to an ear (or portion of an ear) of a user, where the sound-filtering device may be a device such as embodiments of the device 100. For example, the sound-filtering device can include a channel 106 extending between an entry port 102 and an exit port 104 to define a path 107 along which sound travels through the device 100 when the device is coupled to an ear 50 of a user 52, and can further include a resonant chamber 110 offset from the path 107 defined by the channel 106 and in fluid communication with the channel 106 via a side port 108, the resonant chamber 110 being configured to attenuate a frequency at which the user experiences tinnitus. The method can further include a stage of decoupling the sound-filtering device from the ear of the user after a period of use and a stage of repeating said coupling and decoupling multiple times.

In some instances, the period of use is at least 0.5 hours and the insertion and removal of the device is repeated no fewer than 30 times. Other periods of use and insertion/removal repetitions are also contemplated, and these may be determined by a particular treatment regimen. In some instances, the method can include adjusting a geometric volume of the resonant chamber prior to a first coupling of the sound-filtering device to the ear of the user.

Figure 7:
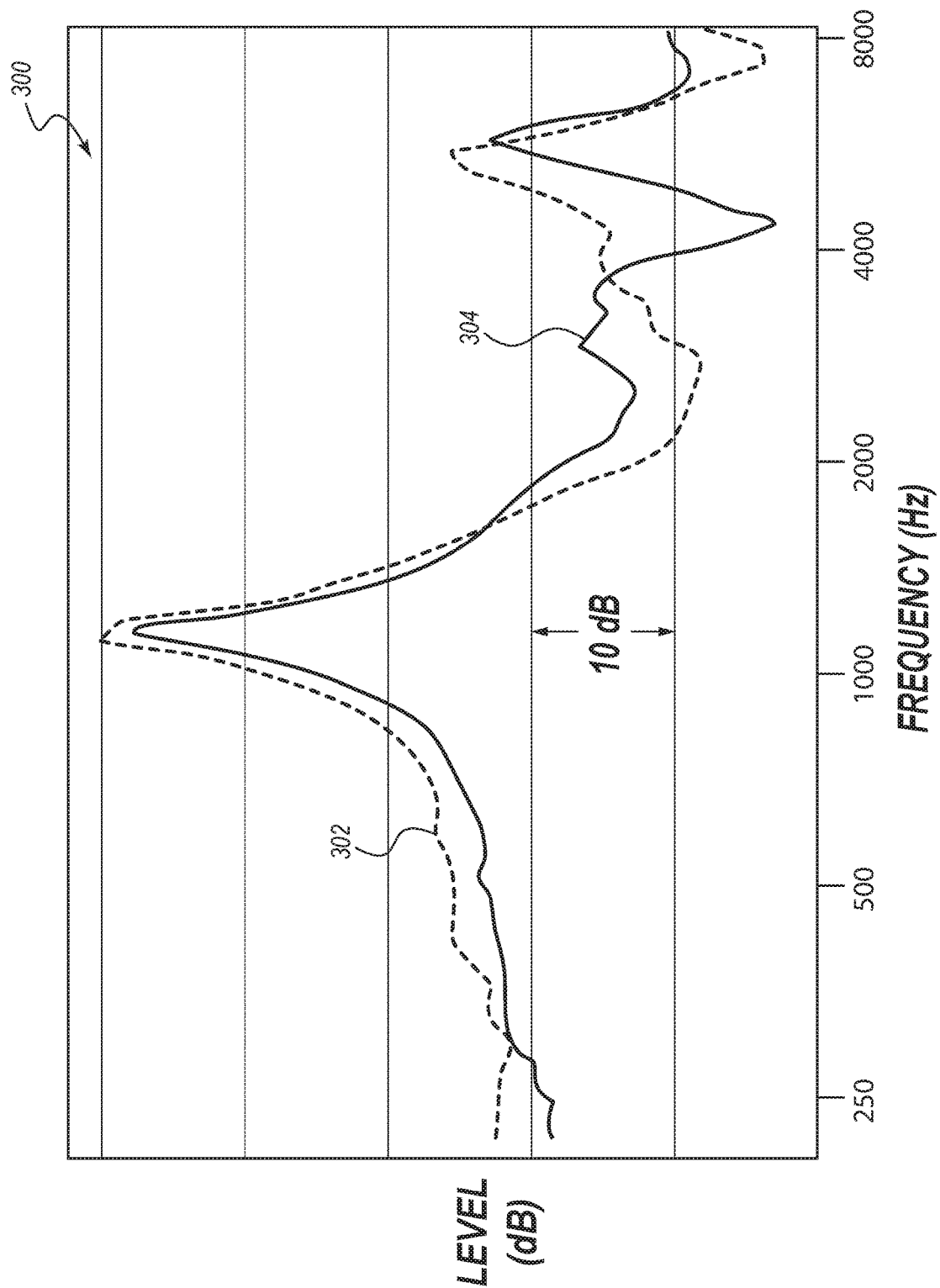
FIG. 7 is a plot depicting an illustrative example of two frequency profiles of sound delivered to an eardrum of a user, wherein the frequency profile depicted as a broken line represents unaltered sound and the frequency profile depicted as a solid line represents sound that has been filtered by a device such as that depicted in FIG. 1.

FIG. 7 is a plot 300 depicting an illustrative example of two frequency profiles 302, 304 of sound delivered to an eardrum of a user. The frequency profile 302 depicted as a broken line represents unaltered sound, and the frequency profile 304 depicted as a solid line represents sound that has been filtered by a device such as an embodiment of the device 100. An octave is the interval between a first tone and a second tone, where the second tone is double the frequency of the first tone. Accordingly, slightly more than five octaves of the frequency profiles 302, 304 are depicted in FIG. 7.

As can be seen from a comparison of the frequency profiles 302, 304, the device 100 acts as a notch filter that attenuates a narrow band of frequencies. The narrow band of attenuated frequencies is centered at approximately 4,500 Hz, and the band spans a frequency range of less than an octave.

Close inspection of frequency profiles 302, 304 reveals what may appear to be attenuation of the unfiltered sound in the range of from approximately 250 Hz to approximately 1,500 Hz. This apparent attenuation, if it is attenuation, may be due to factors unrelated to the resonance effects of the resonant chamber 110. The attenuation may, for example, result from a smaller portion of sound being admitted through the channel 106, as compared with an unobstructed ear canal 54. Even if it this apparent attenuation in a different frequency range is, in fact, an attenuation, and is somehow related to the presence of a resonant chamber 110 (e.g., due to an increase in mass of the device 100 as a whole), this attenuation is not significant. Indeed, the maximum amount of this attenuation, which occurs around 400 Hz, is less than 5 decibels. In contrast, the attenuation at around 4,500 Hz is greater than 10 decibels. In some instances, a "significant" attenuation may be defined as an attenuation that reduces a sound level by no less than 5, 7.5, 10, 12.5, or 15 decibels. In the present example, it is clear that significant attenuation is achieved over a range of frequencies that is far narrower than the full audible spectrum depicted in FIG. 7.

Figure 8:
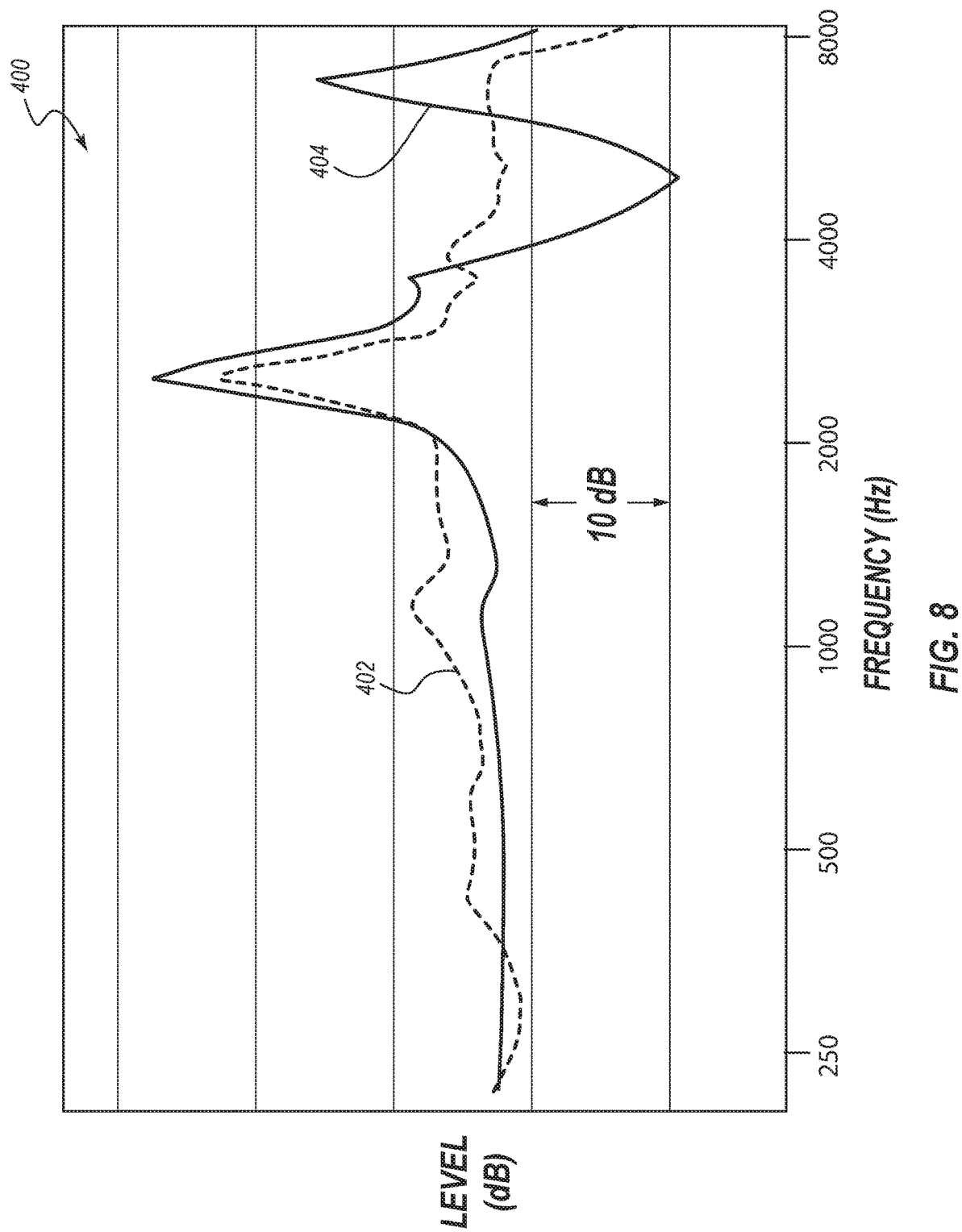
FIG. 8 is a plot depicting another illustrative example of two frequency profiles of sound delivered to an eardrum of a user, wherein the frequency profile depicted as a broken line represents another example of unaltered sound and the frequency profile depicted as a solid line represents sound that has been filtered by another embodiment of a device such as that depicted in FIG. 1 that yields resonant peaks adjacent to upper and lower ends of a band of frequencies that has been attenuated.

FIG. 8 is a plot 400 depicting another illustrative example of two frequency profiles 402, 404 of sound delivered to an eardrum of a user. The frequency profile 402 depicted as a broken line represents another example of unaltered sound, and the frequency profile 404 depicted as a solid line represents sound that has been filtered by another embodiment of a device 100. In this embodiment, the device 100 yields resonant peaks that are adjacent to upper and lower ends of the band of frequencies that has been attenuated, which is again centered at approximately 4,500 Hz. The peaks occur at around 2,000 Hz and around 6,000 Hz.

In some embodiments, the device 100 can be configured to enhance or amplify the volume of the sound adjacent the resonant frequency. For example, the volume can be increased or amplified at frequencies that are near or adjacent to the frequency band that is being attenuated. In particular embodiments, the device amplifies sound passing through the channel at frequencies adjacent to a lower end of the band of frequencies to be attenuated and/or at frequencies adjacent to an upper end of the band of frequencies to be attenuated, as shown in FIG. 8.

Figure 9:
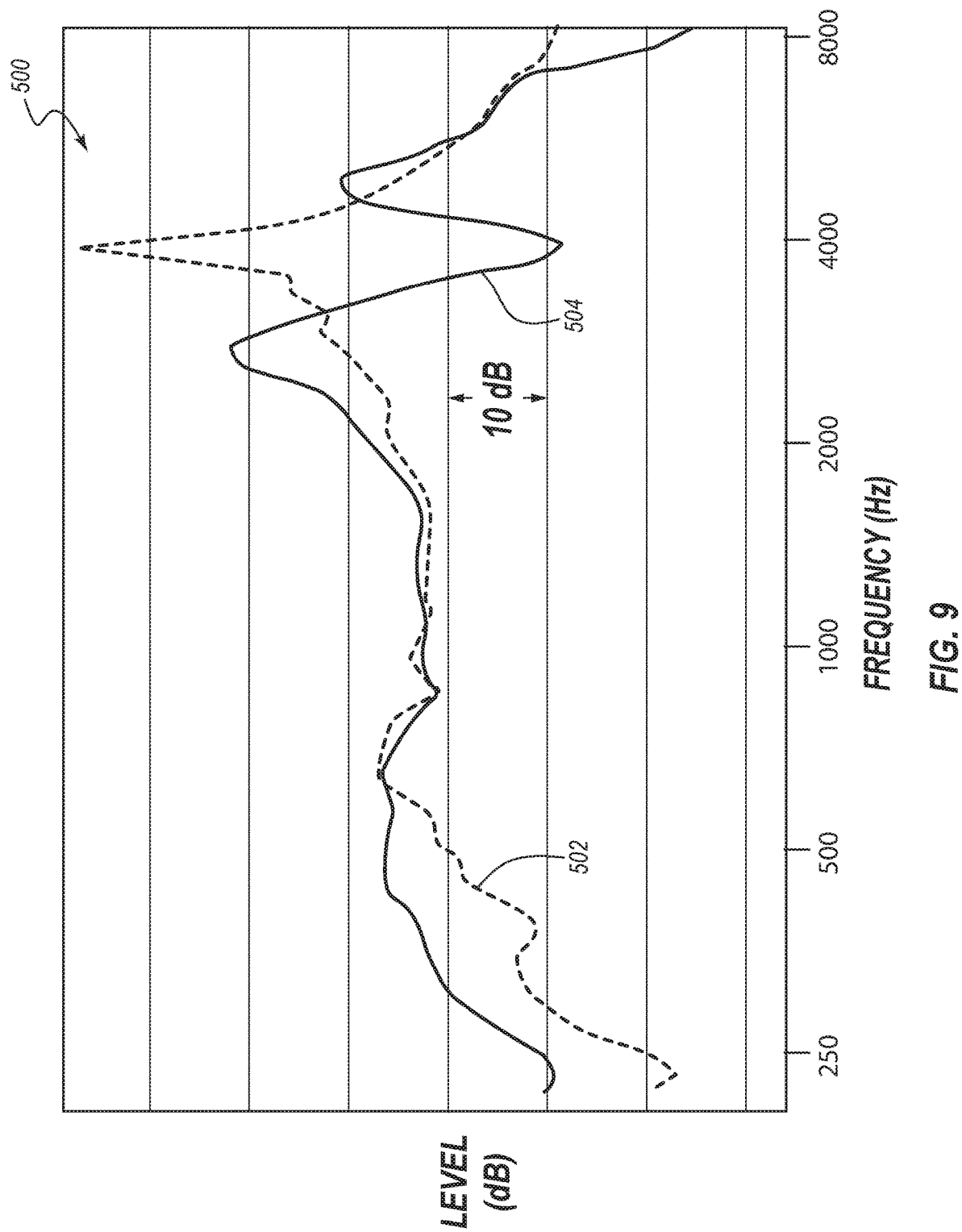
FIG. 9 is a plot depicting another illustrative example of two frequency profiles of sound delivered to an eardrum of a user, wherein the frequency profile depicted as a broken line represents an example of sound that has been passed through a hearing aid that yields feedback and the frequency profile depicted as a solid line represents sound that has been filtered by another embodiment of a device such as that depicted in FIG. 1 that removes the feedback.

FIG. 9 is a plot 500 depicting another illustrative example of two frequency profiles 502, 504 of sound delivered to an eardrum of a user. The frequency profile 502 depicted as a broken line represents an example of sound that has been passed through a hearing aid that yields feedback. The frequency profile 504 depicted as a solid line represents sound that has been filtered by another embodiment of a device 100 that is coupled with the hearing aid and removes the feedback. In some instances, the entry port 102 of the device 100 is coupled to an output of the hearing aid. In other instances, the exit port 104 of the device 100 is coupled to an input of the hearing aid.

Figure 10:
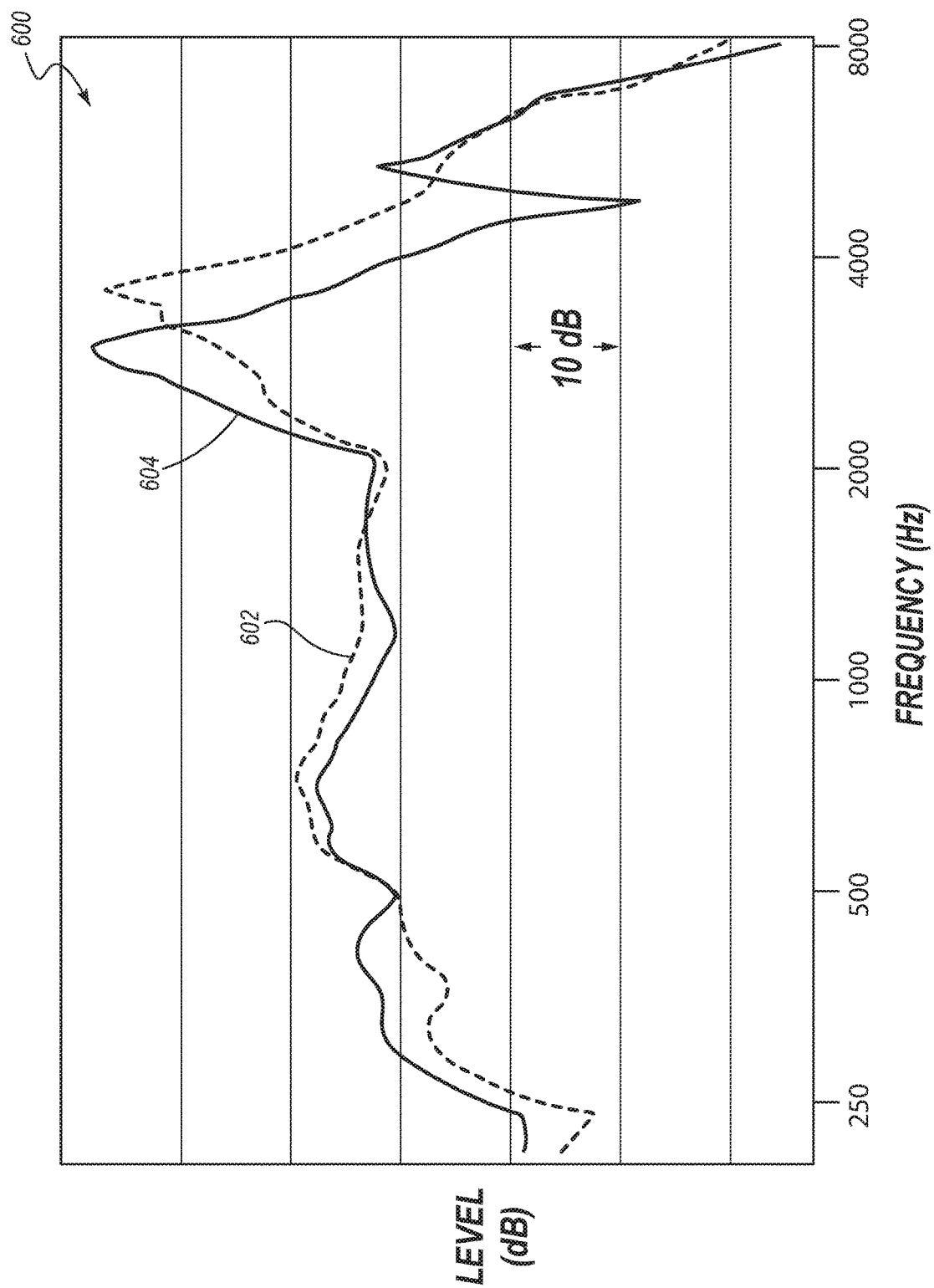
FIG. 10 is a plot depicting another illustrative example of two frequency profiles of sound delivered to an eardrum of a user, wherein both frequency profiles depict sound that is passed through an embodiment of a device such as that depicted in FIG. 1 that is coupled with an embodiment of a hearing aid, wherein the frequency profile depicted as a broken line is generated when a resonant chamber is removed from the device and the solid line is generated when the resonant chamber is coupled to the device.

FIG. 10 is a plot 600 depicting another illustrative example of two frequency profiles 602, 604 of sound delivered to an eardrum of a user. Both frequency profiles 602, 604 depict sound that is passed through an embodiment of a device 100 that is coupled with an embodiment of a hearing aid. The frequency profile 602 depicted as a broken line is generated when a resonant chamber is removed from the device (see FIGS. 13A and 13B and related discussion). The solid line is generated when the resonant chamber is coupled to the device. Notch filtering centered at approximately 4,500 Hz is clearly achieved by use of the resonant chamber.

Figure 11:
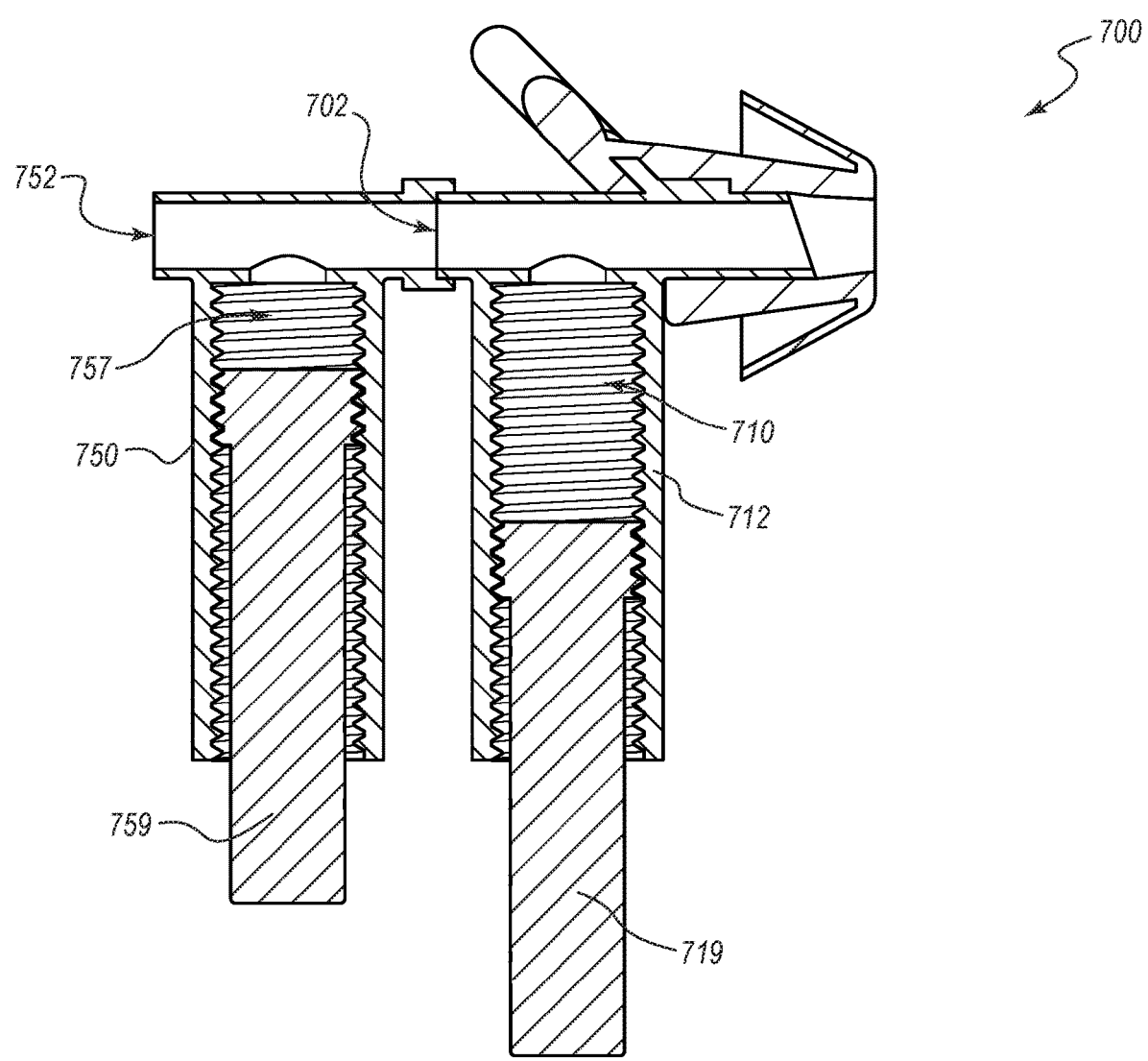
FIG. 11 is a cross-sectional view of another embodiment of a sound-filtering device that is configured to attenuate two narrow bands of frequencies.

FIG. 11 is a cross-sectional view of another embodiment of a sound-filtering device 700 that resembles the device 100 in many respects. Accordingly, like features are designated with like reference numerals, with the leading digits incremented to "7." Relevant disclosure set forth above regarding similarly identified features thus may not be repeated hereafter. Moreover, specific features of the device 700 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the device 700. Any suitable combination of the features, and variations of the same, described with respect to the device 100 can be employed with the device 700, and vice versa. This pattern of disclosure applies equally to further embodiments depicted in subsequent figures and described hereafter, wherein the leading digits may be further incremented.

A distal portion of the device 700 is substantially the same as embodiments of the device 100 described above, and can include an entry port 702, such as the entry port 102, that is defined by a housing element 712. The device 700 further includes a housing element 750 that is selectively attachable to and detachable from a proximal end of the housing element 712. Any suitable connection interface between the housing elements 712, 750 is contemplated. In other embodiments, the housing element 750 is instead permanently attached to the housing element 712. The housing element 750 defines an entry port 752.

Each housing element 712, 750 can be coupled with a separate frequency adjustment member 719, 759 to adjust a geometric volume of a resonant chamber 710, 757 defined by the housing element 712, 750. In some instances, the cavities 710, 757 can be adjusted to different geometric volumes, corresponding to different resonant frequencies, and the device 700 can filter or attenuate two separate bands of frequencies.

Figure 12A:
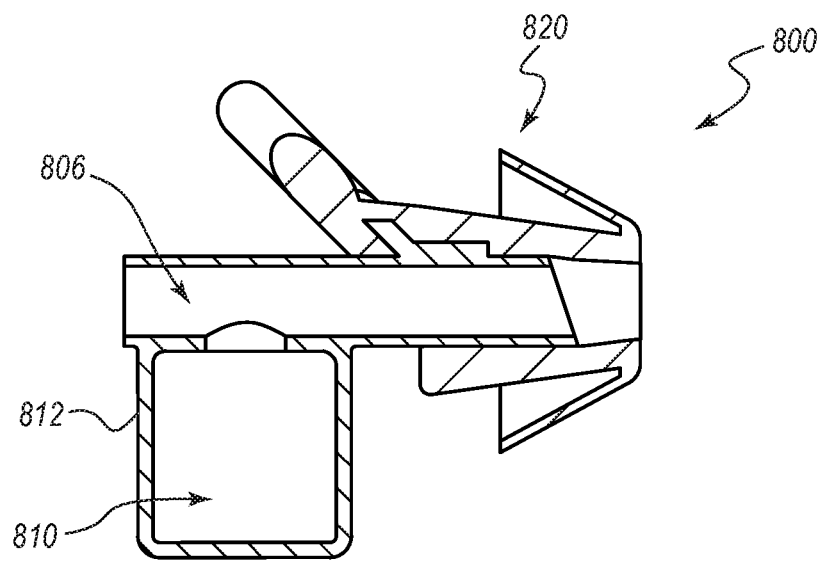
FIG. 12A is a cross-sectional view of another embodiment of a sound-filtering device that includes a fixed-volume resonant chamber.

FIG. 12A is a cross-sectional view of another embodiment of a sound-filtering device 800 that includes a fixed-volume resonant chamber 810. That is, a geometric volume of the resonant chamber 810 is fixed. At least a portion of a channel 806 and an entirety of the resonant chamber 810 are defined by a single housing element 812. The housing element 812 is coupled with an anchoring assembly 820. It will be appreciated that the shape of the fixed-volume resonant chamber 810 can be varied. For example, in some embodiments, the housing element 812 within which the resonant chamber 810 is disposed is cylindrical in shape. Other shapes can also be used, including circular, spherical, or other shapes such as shapes that more closely fit the contours of the ear, including custom shapes. For instance, custom shapes that fit within a portion of the ear can be used to provide a more aesthetic appearance.

Figure 12B:
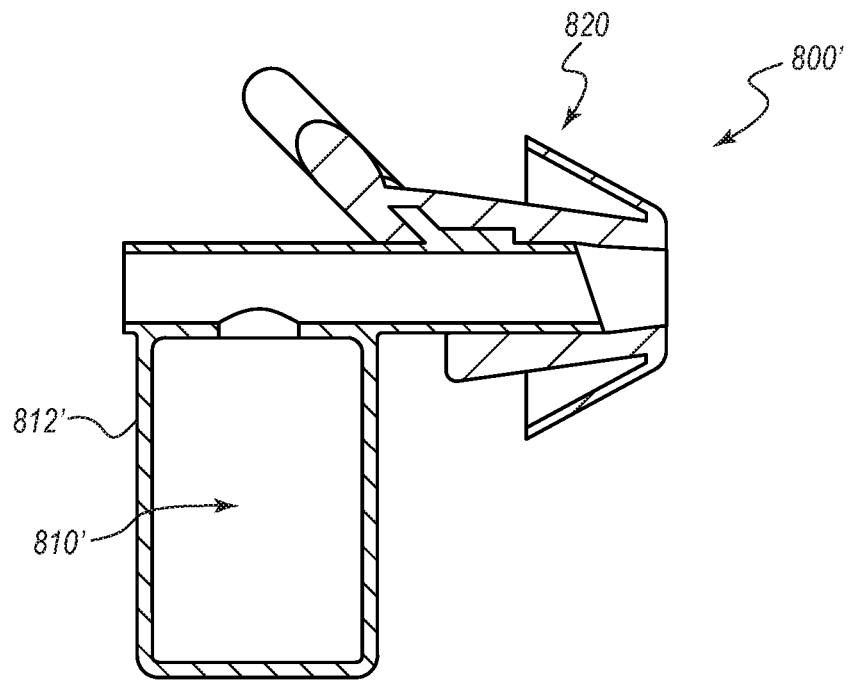
FIG. 12B is a cross-sectional view of another embodiment of a sound-filtering device that includes a fixed-volume resonant chamber.

FIG. 12B is a cross-sectional view of another embodiment of a sound-filtering device 800' that also includes a fixed-volume resonant chamber 810' of a different size defined by a housing element 812'. In some instances, the housing elements 812, 812' may be coupled interchangeably with the anchoring assembly 820.

Figure 13A:
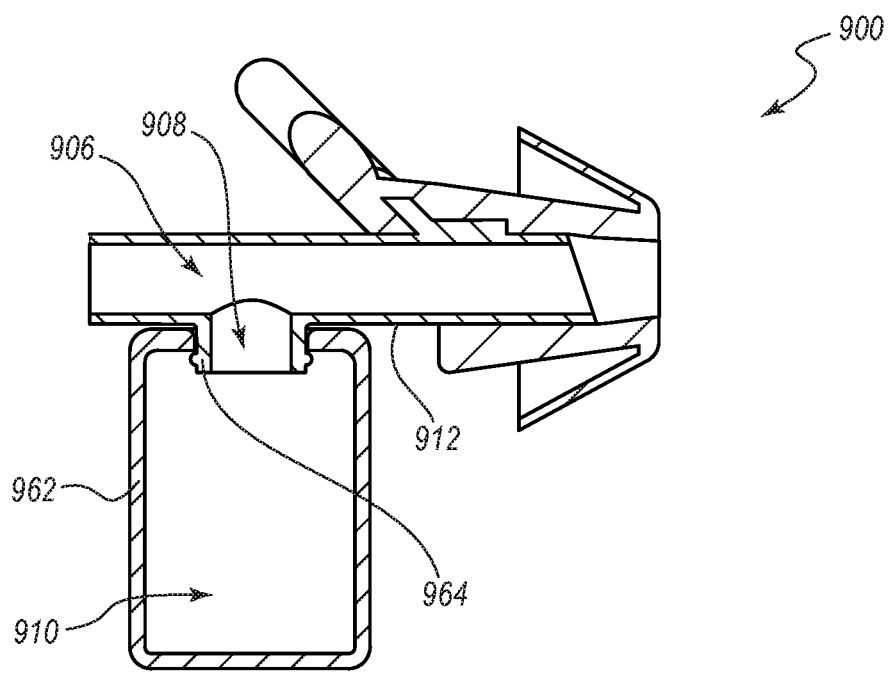
FIG. 13A is a cross-sectional view of another embodiment of a sound-filtering device that includes a selectively attachable and detachable resonant chamber.

FIG. 13A is a cross-sectional view of another embodiment of a sound-filtering device 900 that includes a selectively attachable and detachable resonant chamber 910. A first housing element 912 defines at least a portion of a channel 906 and also defines a side port 908. A second housing element 962 defines at least a portion of the resonant chamber 910. In the illustrated embodiment, the second housing element 962 defines almost an entirety of the resonant chamber 910, but a neck 964 of the first housing element 912 that defines the side port 908 at an interior surface thereof also provides a small sidewall of the resonant chamber 910 at an exterior surface of the neck 964. The second housing element 962 is selectively attachable to and detachable from the first housing element 912 at the neck 964. Any suitable connection interface is contemplated. For example, in the illustrated embodiment, the first and second housing elements 912, 962 are selectively attachable via a snap-fit configuration. In the illustrated embodiment, the second housing element 962 encompasses the side port 908 when attached to the first housing element 912.

In particular embodiments, the parameters of the neck 964, such as the length or diameter, can be modified to adjust the resonant frequency. An adjustment nozzle can also be used with the neck 964, as further detailed below.

Figure 13B:
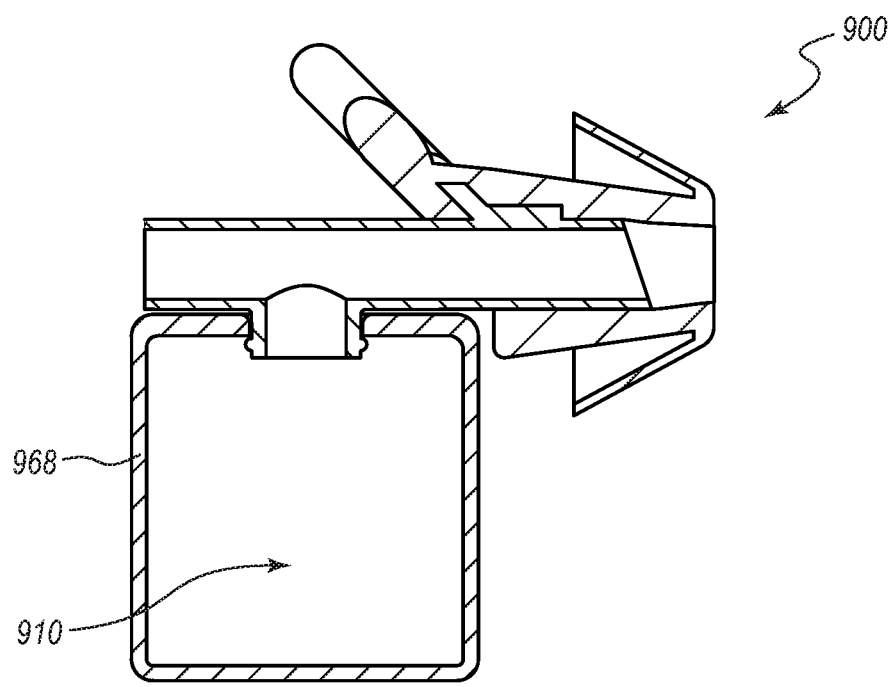
FIG. 13B is a cross-sectional view of the sound-filtering device of FIG. 13A that includes a selectively attachable and detachable resonant chamber having a different geometric volume than that of the resonant chamber depicted in FIG. 13A.

FIG. 13B is a cross-sectional view of the sound-filtering device 900 in a different volumetric state than that shown in FIG. 13A. In particular, a geometric volume of the resonant chamber 910 has been altered by replacing the second housing element 962 with a differently sized third housing element 968. As can be appreciated, the size of the housing element 962 can be selected based on a desired resonant frequency.

Figure 14A:
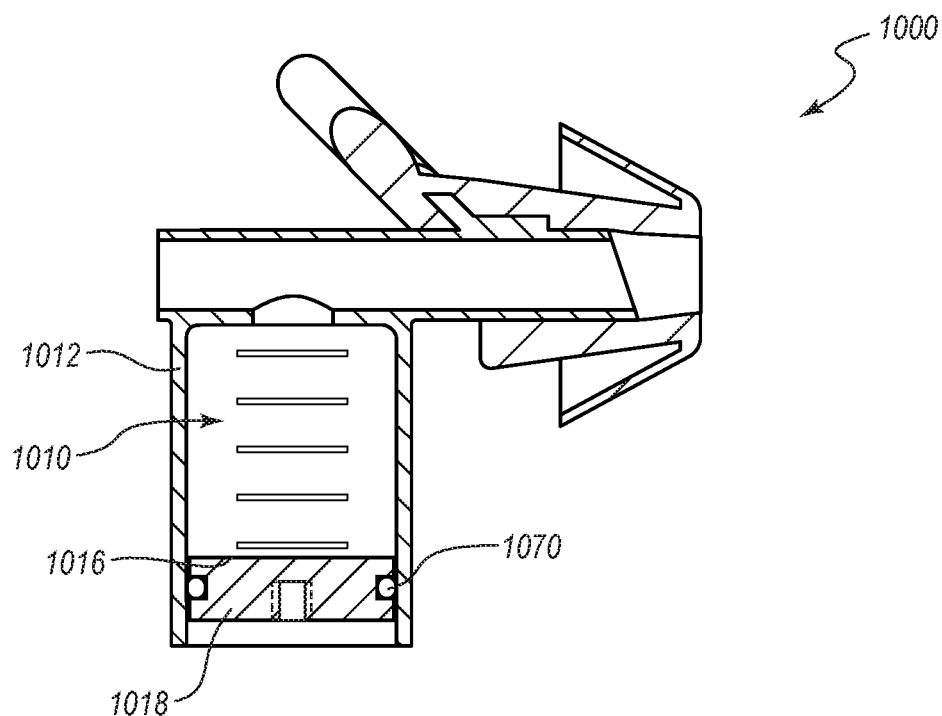
FIG. 14A is a cross-sectional view of another embodiment of a sound-filtering device that includes a size-adjustable resonant chamber.

FIG. 14A is a cross-sectional view of another embodiment of a sound-filtering device 1000 that includes a size-adjustable resonant chamber 1010. The device 1000 includes a housing element 1012 that defines a portion of the resonant chamber 1010, and further includes an end wall 1016, such as a piston 1018, that defines a proximal end of the resonant chamber 1010. In the illustrated embodiment, the device 1000 includes a sealing element 1070, such as an O-ring or other sealing member, that is disposed between the end wall 1016 and the housing element 1012. The sealing element 1070 can define a fluid-tight seal at a proximal end of the resonant chamber 1010 to close the resonant chamber 1010. The sealing element 1070 can also serve to maintain the end wall 1016 in a fixed relationship relative to the housing element 1012.

Figure 14B:
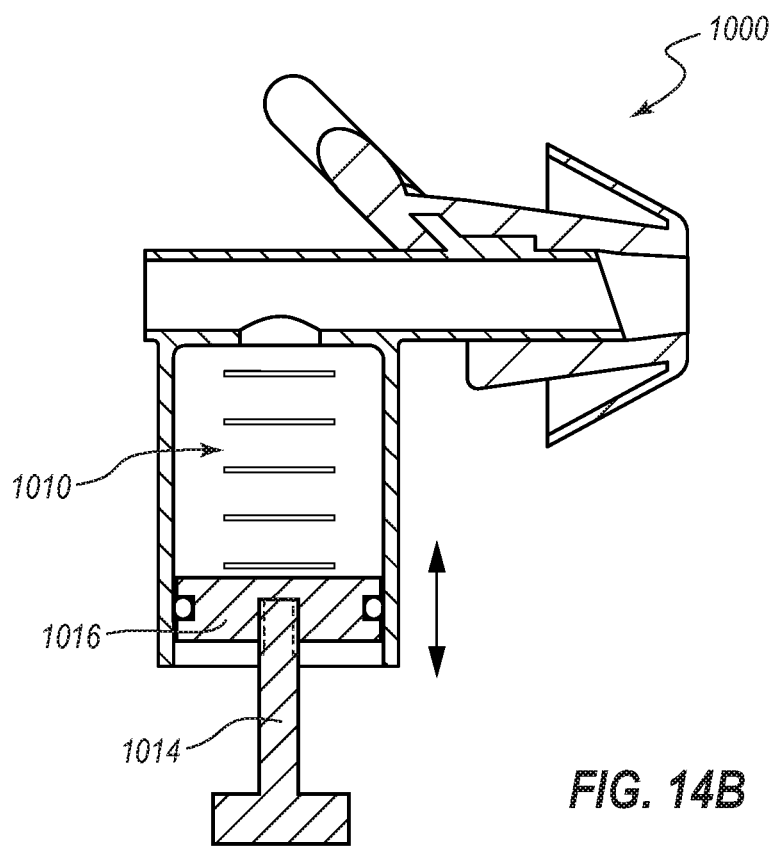
FIG. 14B is a cross-sectional view of the sound-filtering device of FIG. 14A with a post coupled to a cap to adjust a size of the resonant chamber.

FIG. 14B is a cross-sectional view of the sound-filtering device 1000 with a post 1014 coupled to the end wall 1016. When coupled with the end wall 1016, the post 1014 can be manipulated to adjust a size of the resonant chamber 1010. In some embodiments, the post 1014 is selectively attachable to and detachable from the end wall 1016. Any suitable connection interface is contemplated. In other embodiments, the post 1014 may be secured to the end wall 1016 in an initial state, and then once a desired size of the resonant chamber 1010 is achieved, the post 1014 can be irreversibly detached from the end wall 1016. For example, the end wall 1016 and the post 1014 can be formed of a unitary piece of material, and once the desired setting of the end wall 1016 is achieved, the post 1014 can be snapped off, twisted off, or otherwise removed from the end wall 1016.

Figure 15:
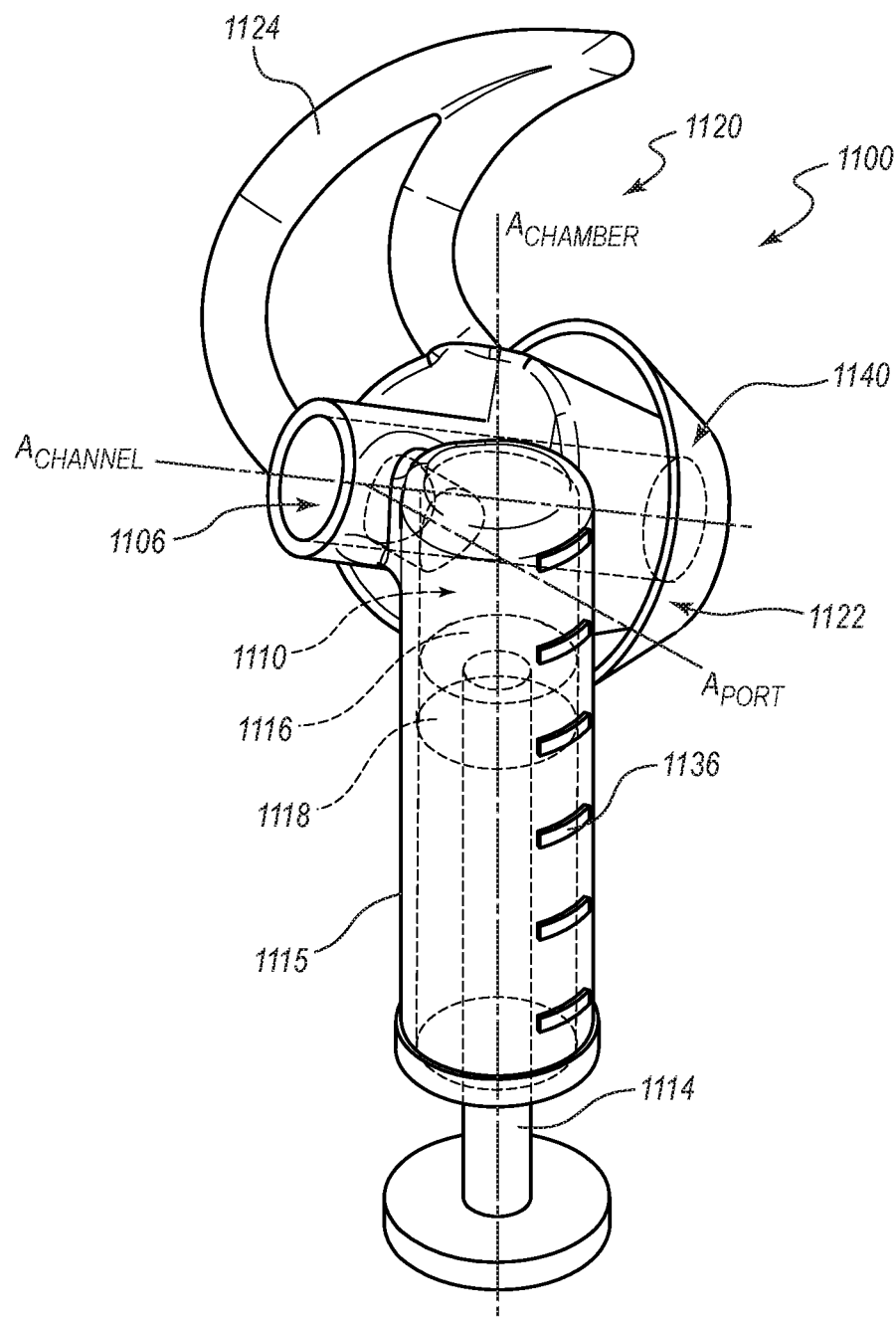
FIG. 15 is a perspective view of another embodiment of a sound-filtering device that includes a size-adjustable resonant chamber.
Figure 16:
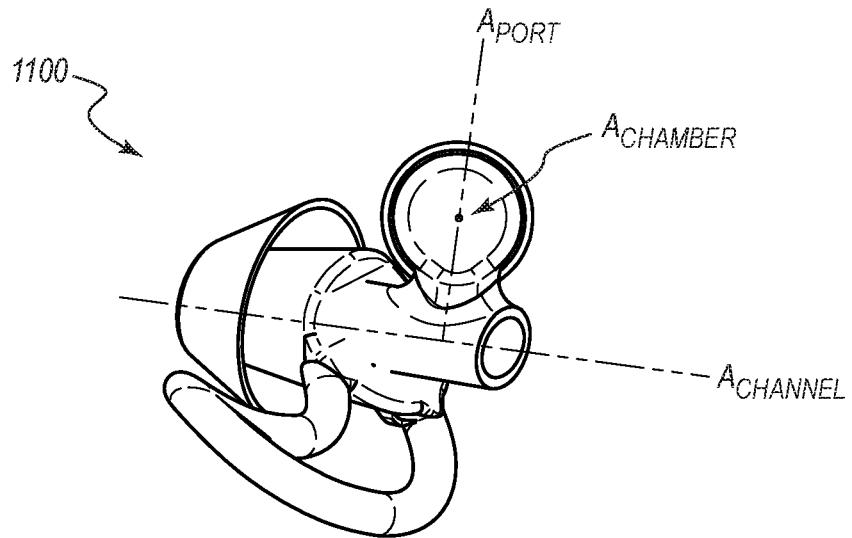
FIG. 16 is a top plan view of the sound-filtering device of FIG. 15.
Figure 17:
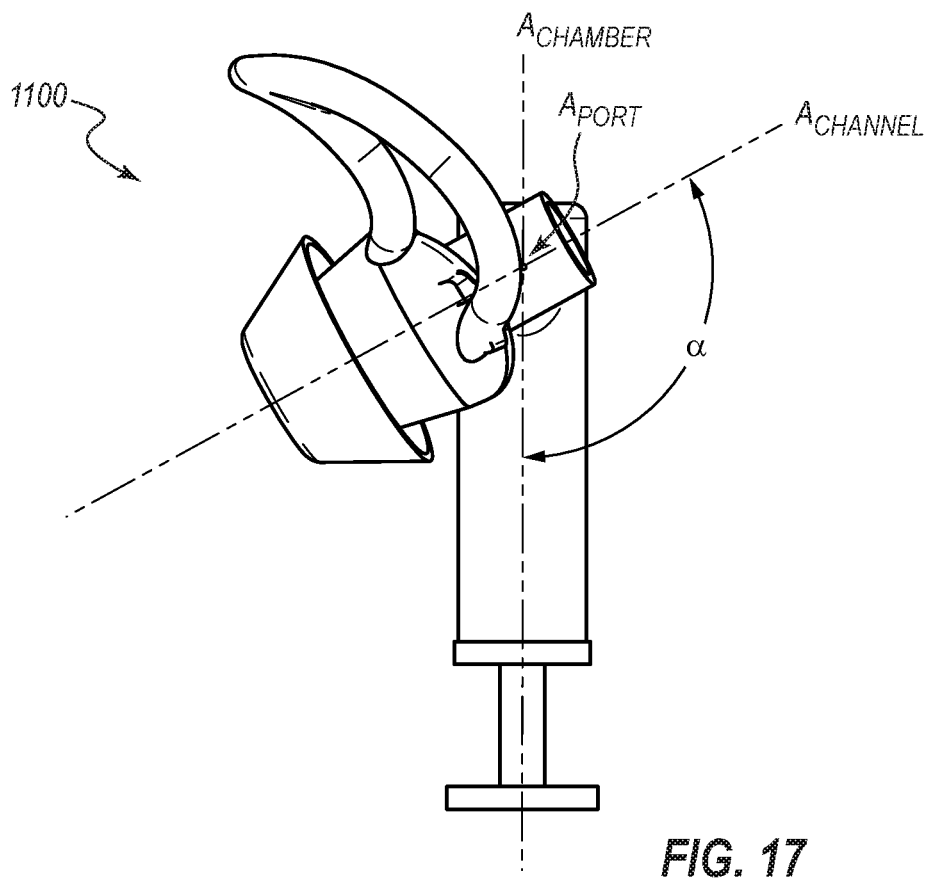
FIG. 17 is a side elevation view of the sound-filtering device of FIG. 15.

FIGS. 15-18 are various views of another embodiment of a sound-filtering device 1100 that includes a size-adjustable resonant chamber 1110. The device 1100 includes a channel 1106 that defines a longitudinal axis $A_{CHANNEL}$ that is configured to be directed into the ear canal of the ear when the device 1100 is worn. A side port defines a central axis $A_{PORT}$, and the resonant chamber 1110 defines a longitudinal axis $A_{CHAMBER}$. The resonant chamber 1110 is offset from the channel 1106. As seen in FIG. 16, the longitudinal axes $A_{CHANNEL}$, $A_{CHAMBER}$ are spaced from each other and do not intersect. As seen in FIG. 17, the longitudinal axes $A_{CHANNEL}$, $A_{CHAMBER}$ are rotated relative to each other through an oblique angle α. In some embodiments, the angle α may be zero (e.g., the longitudinal axes $A_{CHANNEL}$, $A_{CHAMBER}$ may be parallel). In the illustrated embodiment, the longitudinal axis $A_{CHAMBER}$ of the resonant chamber 1110 is directed substantially vertically when the device 1100 is coupled to the ear of the user and the head of the user is in an upright orientation. In some embodiments, the longitudinal axis $A_{CHAMBER}$ of the resonant chamber 1110 is substantially parallel to a cheek of the user when the device 1100 is coupled to the ear of the user.

Figure 18:
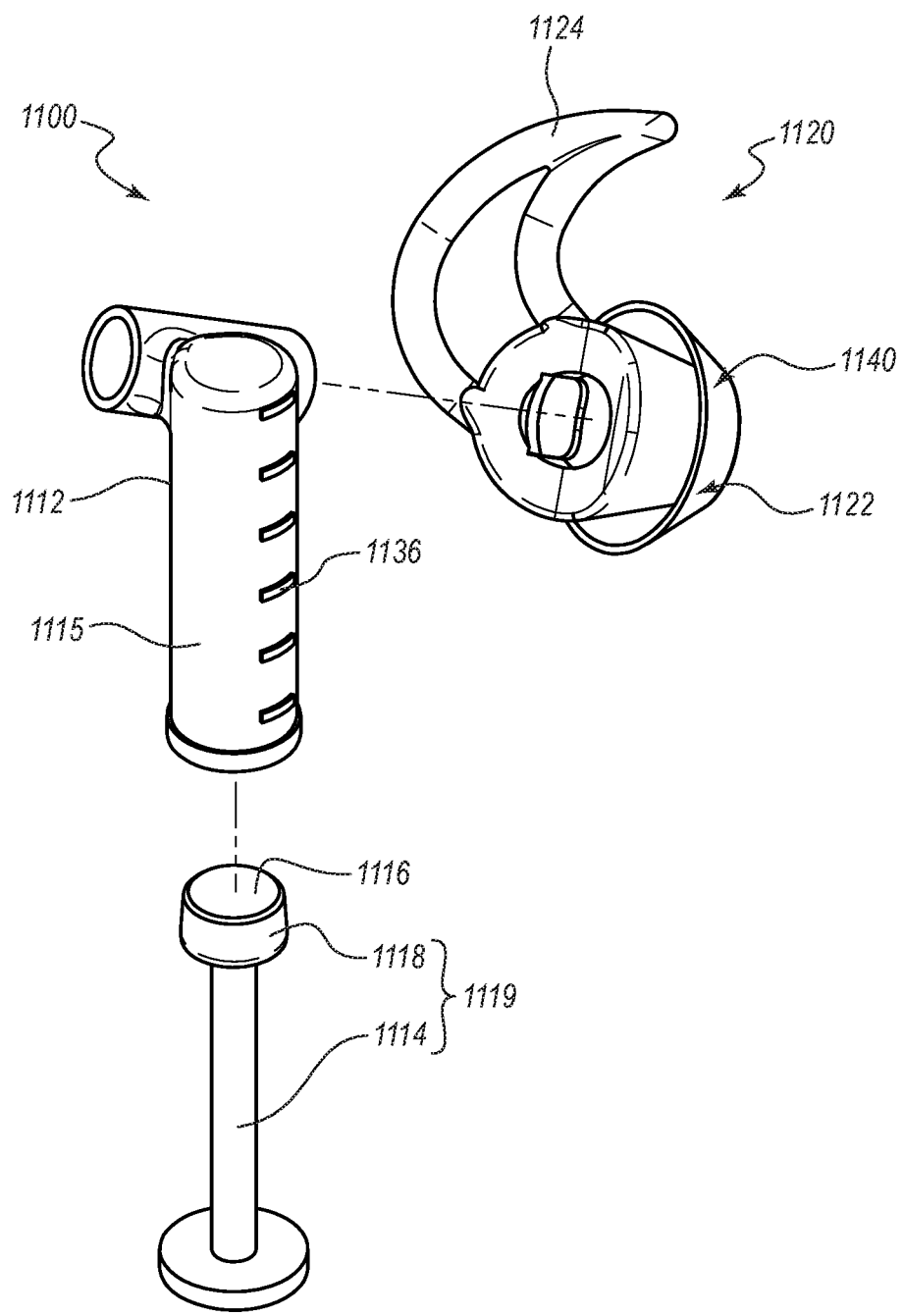
FIG. 18 is an exploded perspective view of the sound-filtering device of FIG. 15.

With continued reference to FIGS. 15 and 18, the anchoring system 1120 of the device 1100 includes an insert portion 1122 comprising a resilient member 1140. The anchoring system 1120 also includes an anchoring arm or member 1124 configured to aid in securing the device 1100 to a user's ear. In the illustrated embodiment, the anchoring arm or member 1124 is shaped to fit within the contour of a user's ear. Other shapes and/or configurations are also contemplated.

Further, in some embodiments, the anchoring system 1120, which includes an anchoring arm or member 1124, is removable or capable of being uncoupled from the housing element 1112. In such embodiments, different anchoring systems 1120 can be used. For example, anchoring systems 1120 having different sized anchoring arms or members 1124 can be used depending on the size and/or shape of the user's ear. In yet other embodiments, the anchoring arm or member 1124 of the anchoring system 1120 can be custom molded to fit within a user's ear. Such a custom molded anchoring arm or member 1124 can be coupled to the housing element 1112 prior to use.

In some embodiments, the resonant chamber 1110 can include markings 1136 on the outer surface of the sidewall 1115 of the housing element 1112. Such markings 1136 can correspond to settings of different volumetric states of the resonant chamber 1110. As previously discussed, different volumetric states can correspond to different frequency attenuation settings.

In some of such embodiments, at least a portion of the housing element 1112 may be at least partially transparent such that the frequency adjustment member 1119 can be visible through at least a portion of the housing element 1112. For example, the end wall 1116 of the piston 1118 can be observed through at least a portion of the housing element 1112. Further, the frequency adjustment member 1119 comprises a post 1114 to aid in manipulating the end wall 1116 to adjust the geometric volume of the resonant chamber 1110.

Figure 19:
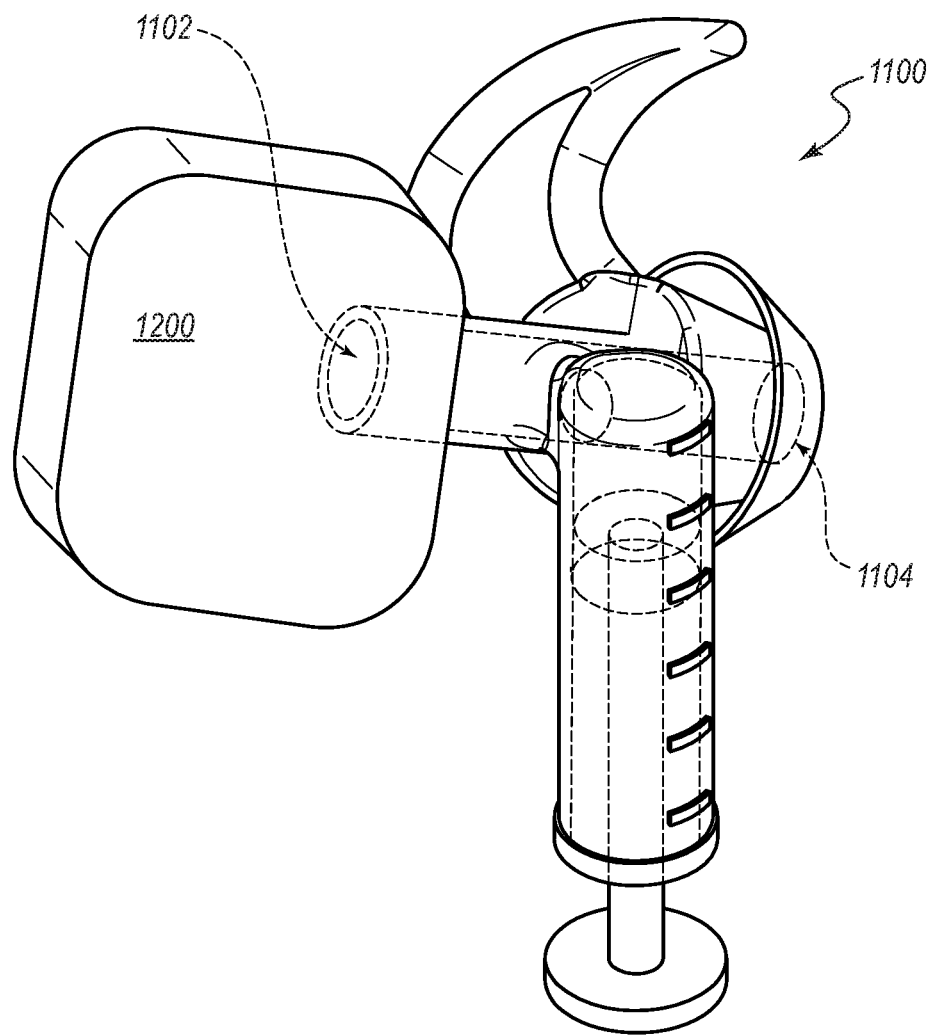
FIG. 19 is a perspective view of the sound-filtering device of FIG. 15 coupled with a hearing aid.

FIG. 19 is a perspective view of an embodiment of the sound-filtering device 1100 coupled with a hearing aid 1200. In the illustrated arrangement, an output of the hearing aid 1200 is coupled to an entry port 1102 of the device 1100. In other arrangements, an exit port 1104 of the device 1100 can be coupled to an input of the hearing aid 1200.

Figure 20:
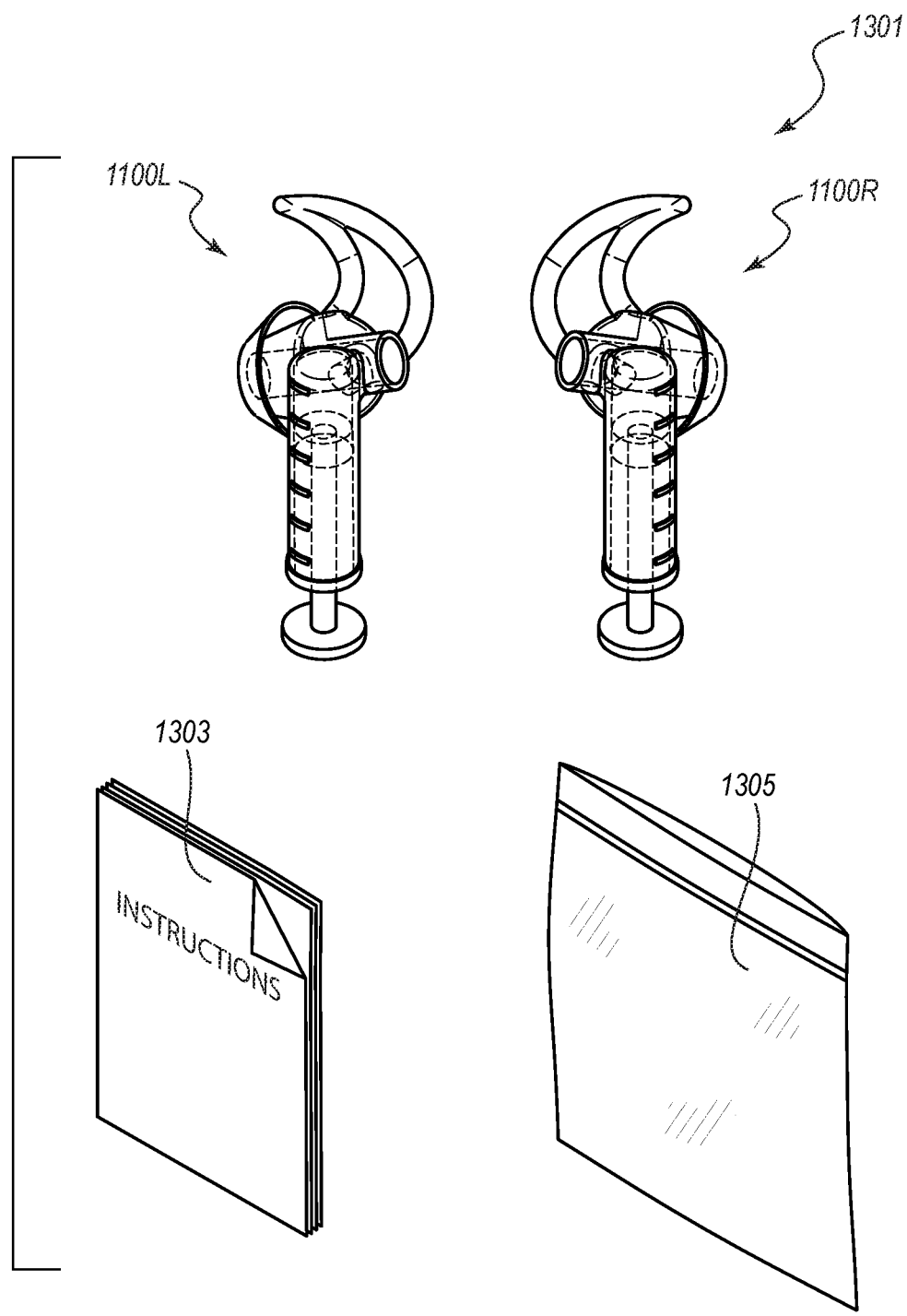
FIG. 20 is a perspective view of an embodiment of a kit that includes a left-ear oriented sound-filtering device and a right-ear oriented sound-filtering device.

FIG. 20 is a perspective view of an embodiment of a kit 1301 that includes a left-ear oriented sound-filtering device 1301L and a right-ear oriented sound-filtering device 1100R. The kit 1301 can further include instructions 1303. The instructions 1303 can include directions for performing any and/or all of the steps of one or more of the methods discussed herein. The method steps include any specifically described above, implied from the disclosure herein, or specifically recited in the appended claims. In other or further embodiments, the instructions 1303 may provide directions for accessing such directions. For example, the instructions 1303 may list a web address, a mailing address, and/or a telephone number that can be used to locate instructions for assembling or using one or more of the devices 1100L, 1100R. In some embodiments, the kit 1301 includes packaging 1305, which can include the instructions 1303 therein and/or thereon.

FIGS. 21-24 depict another embodiment of a sound-filtering device 1300. The sound-filtering device 1300 includes an anchoring system 1320 that includes an insert portion 1322 comprising a resilient member 1340. The anchoring system 1320 also includes an anchoring arm or member 1324 that is configured to aid in securing the device 1300 to a user's ear. As previously stated, the anchoring system 1320, including the anchoring arm or member 1324, can be removable or capable of being uncoupled from the housing element 1312. In other embodiments, the anchoring system 1320, including the anchoring arm or member 1324, can be integral with the housing element 1312.

In certain embodiments, anchoring systems 1320 having different anchoring arms or members 1324 can also be used. For example, different sized anchoring arms or members 1324 can be used depending on the size and/or shape of the user's ear. In yet other embodiments, the anchoring arm or member 1324 can be custom molded.

As shown in the illustrated embodiment, in some instances, the channel 1306 that passes through the housing element 1312 to the ear of the user need not be linear or rectilinear. Rather, the channel 1306 can be curved depending on the size and/or shape of the device 1300.

In the illustrated embodiment, the housing element 1312 comprises an internal adjustment interface 1330, and the end wall of the piston or cap 1318 (which can also be referred to as a frequency adjustment member 1319) defines an external adjustment interface 1332 that cooperates with the internal adjustment interface 1130 to effect adjustment of the geometric volume of the resonant chamber 1310. For example, the location of the end wall 1316 with respect to the sidewall 1315 of the housing element 1312 can be adjusted by rotating, twisting, or otherwise screwing the frequency adjustment member 1319. In some of such embodiments, the frequency adjustment member 1319 comprises a screw.

Figure 30:
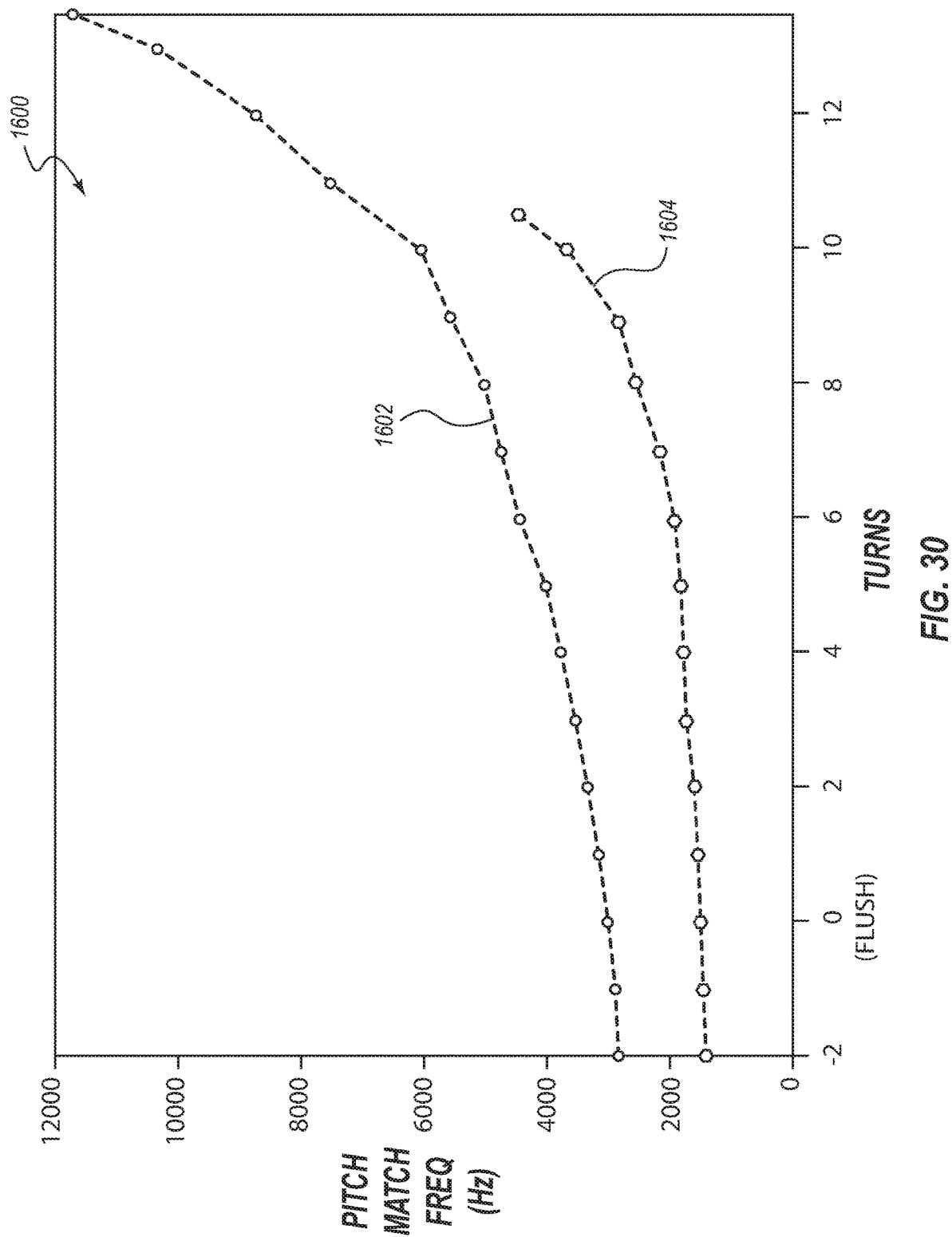
FIG. 30 is a plot depicting illustrative examples of resonant frequency tuning profiles of an adjustable sound-filtering device, wherein the resonant frequency tuning profile with the higher frequency represents a profile generated by a device such as that depicted in FIG. 21, and the resonant frequency tuning profile with the lower frequency represents a profile generated by using an adjustment nozzle with the device, such as is depicted in FIG. 24.

In certain embodiments, the device 1300 can include instructions, such as a chart or graph, illustrating the relationship between the location of the frequency adjustment member 1319 and the frequency range to be attenuated. For example, the frequency adjustment member 1319 may attenuate a certain frequency band when it is at a first or flush position adjacent the proximal end of the housing element 1312 (the end furthest away from the side port 1308 into the channel 1306). The geometric volume of the resonant chamber 1310 can be adjusted as the frequency adjustment member 1319 is rotated, twisted, or screwed in the direction towards (or away from) the side port 1308. In some of such embodiments, a chart or graph can indicate the target frequency (resonant frequency or frequency at which maximum attenuation is achieved) to be attenuated that is associated with each full turn (360 degrees) or partial turn of the frequency adjustment member 1319. Such a chart or graph can aid in tuning the device 1300 to a desired resonant frequency. An exemplary plot is shown in FIG. 30 and further described below.

In further embodiments, the device 1300 can be tuned by the addition of an adjustment nozzle 1380. For example, the resonant frequency can be adjusted by changing the size and/or shape of the side port 1308 from the channel 1306 into the resonant chamber 1110. In some embodiments, the size and/or shape of the side port 1308 can be modified using an adjustment nozzle 1380.

As shown in the illustrated embodiment of FIG. 24, an adjustment nozzle 1380 can be coupled to the housing 1312. For example, an adjustment nozzle 1380 can include an external adjustment interface 1385 that can cooperate with the internal adjustment interface 1330 of the housing element 1312. When disposed at or adjacent the neck 1364 of the housing element 1312, the size and/or shape of the side port 1308 can be modified. For example, the diameter or size of the side port 1308 in FIG. 24 has been reduced with the addition of the adjustment nozzle 1380 in comparison to the unobstructed side port 1308 depicted in FIG. 23. More specifically, a portion 1382 of the adjustment nozzle 1380 has been disposed along the neck 1364 of the housing 1312 to reduce the diameter or size of the side port 1308.

Figure 21:
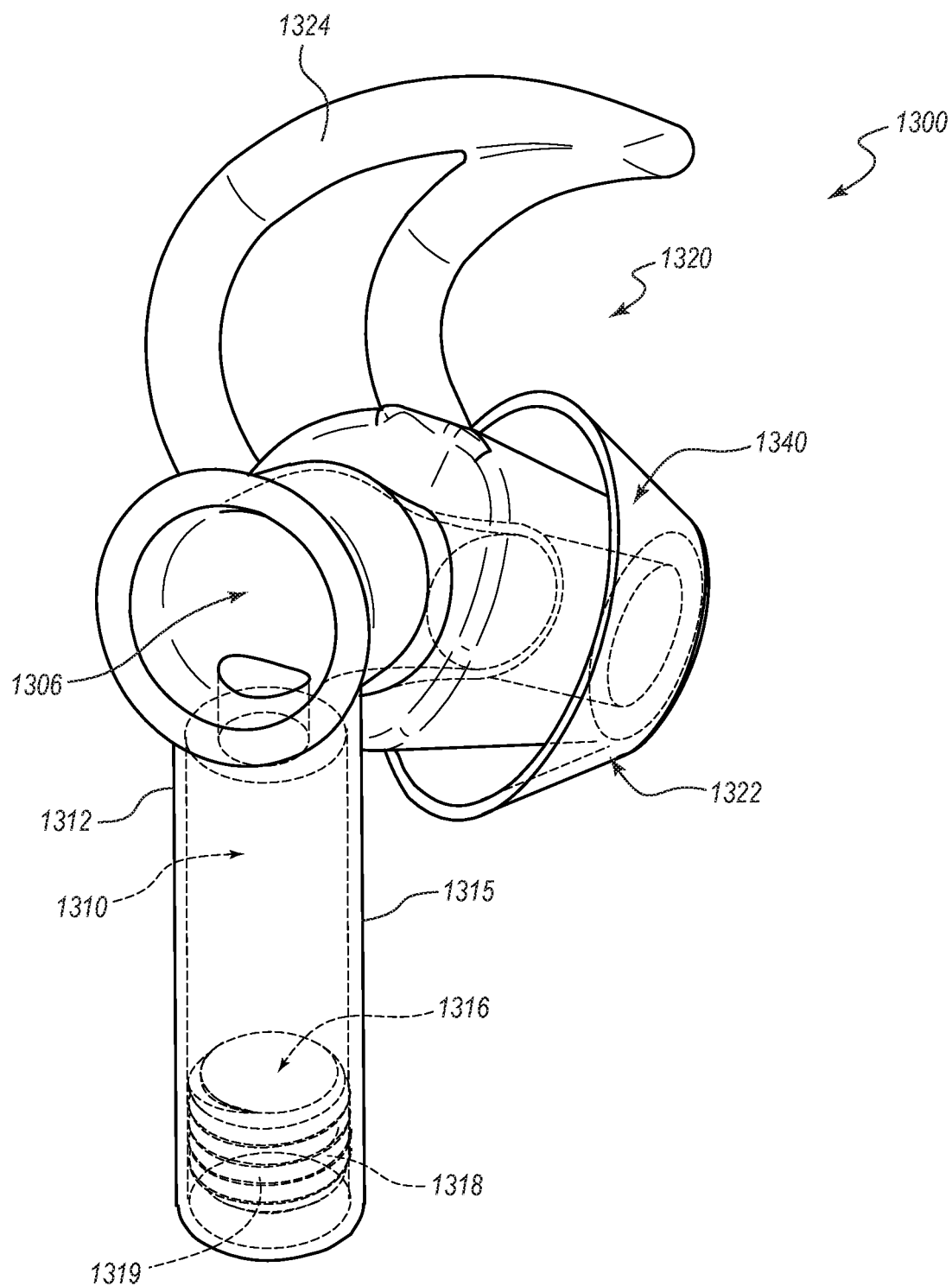
FIG. 21 is a perspective view of another embodiment of a sound-filtering device.
Figure 22:
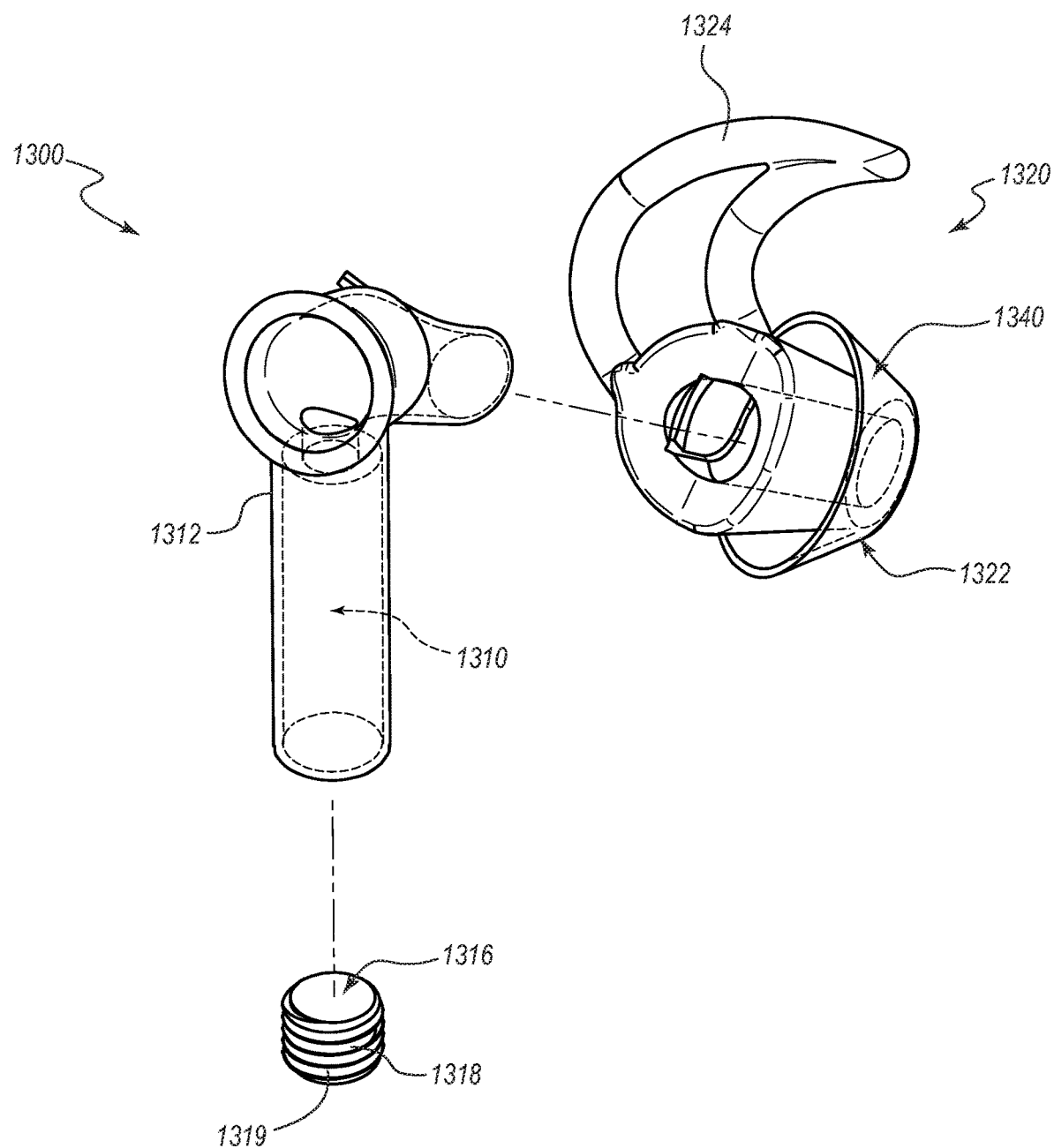
FIG. 22 is an exploded perspective view of the sound-filtering device of FIG. 21.
Figure 25:
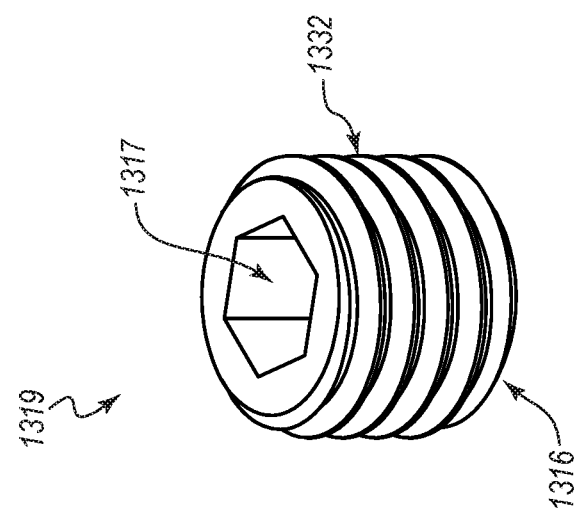
FIG. 25 is a perspective view of a frequency adjustment member used in connection with the sound-filtering device of FIG. 21.

FIG. 25 is a perspective view of the frequency adjustment member 1319 of FIGS. 21-14. In the illustrated embodiment, the frequency adjustment member 1319 comprises a screw that includes an external adjustment interface 1332. The frequency adjustment member 1319 has been inverted such that the end wall 1316 is facing downward to illustrate an internal adjustment interface 1317. Various types of internal adjustment interfaces 1317 can be used with the frequency adjustment member 1319. For example, in some embodiments, the internal adjustment interface 1317 of the frequency adjustment member 1319 comprises a recess or protrusion that is compatible with a keyed tool, such as a hex key or Allen wrench. In other embodiments, the internal adjustment interface 1317 of the frequency adjustment member 1319 comprises a slotted recess such that it is compatible with a slotted screwdriver or tool, or the internal adjustment interface 1317 of the frequency adjustment member 1319 comprises a cross-recess such that it is compatible with a Phillips screwdriver or tool. Other types of keyed or shaped recesses are also contemplated, including star shaped recesses and uniquely shaped recesses. The internal adjustment interface 1317 can also comprise a protrusion (or keyed protrusion). It will thus be contemplated that any type of recess (or protrusion) and key can be employed with the frequency adjustment member 1319. The key or tool can also be inserted at any time to adjust the resonant frequency, after which the key or tool can be removed.

Figure 26B:
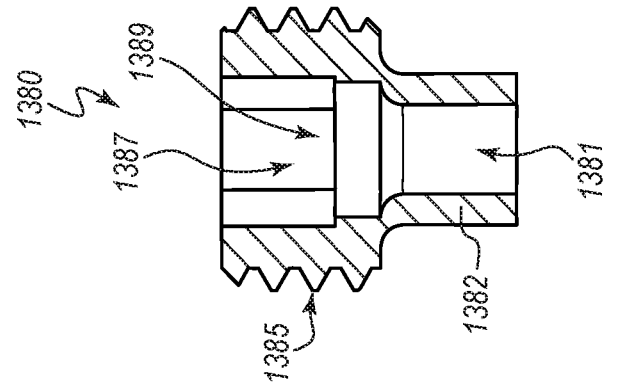
FIG. 26B is a cross-sectional view of the adjustable nozzle of FIG. 26A taken along the view line 26B-26B in FIG. 26A.
Figure 26A:
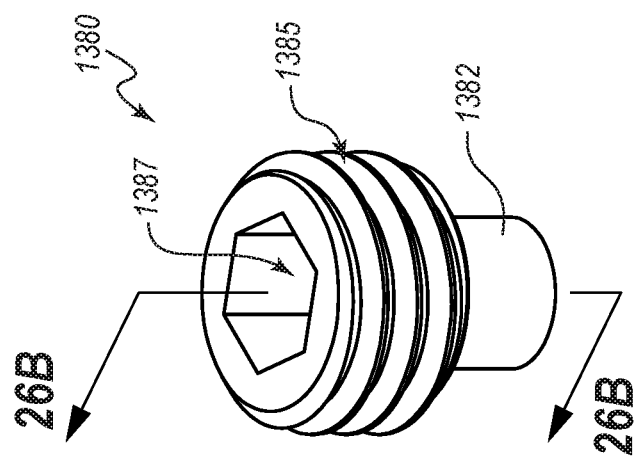
FIG. 26A is a perspective view of an adjustable nozzle used in connection with the sound-filtering device of FIG. 24.

FIGS. 26A and 26B depict the adjustment nozzle 1380. In the illustrated embodiment, the adjustment nozzle 1380 comprises a screw that includes an external adjustment interface 1385. The adjustment nozzle 1380 also comprises a portion 1382 that is configured to be disposed along the neck of a housing. The adjustment nozzle 1380 also includes an internal adjustment interface 1387. Like the frequency adjustment member 1319 depicted in FIG. 25, any variety of internal adjustment interfaces 1387 can be employed such as hex keys or Allen wrenches.

In the cross-sectional view of FIG. 26B, a port 1381 is also depicted in the adjustment nozzle 1380. When employed with a sound-filtering device, such as the sound-filtering device 1300 depicted in FIGS. 21-24, the port 1381 can be aligned with the side port 1308 of the housing 1312. A lumen or passageway 1389 also extends through the adjustment nozzle 1380, from the port 1381 to the internal adjustment interface 1387.

FIGS. 27A and 27B depict a perspective view of another embodiment of a sound-filtering device 1400. In the illustrated embodiment, the sound-filtering device is coupled with a hearing aid. In particular, an output 1204 (e.g., a speaker) of a hearing aid can be coupled via a coupling mechanism 1202 to an entry port 1402 of the housing element 1412 of the device 1400. The output 1204 can also be disposed adjacent to the side port 1408 such that sound from the output 1204 passes over the side port 1408.

Figure 29:
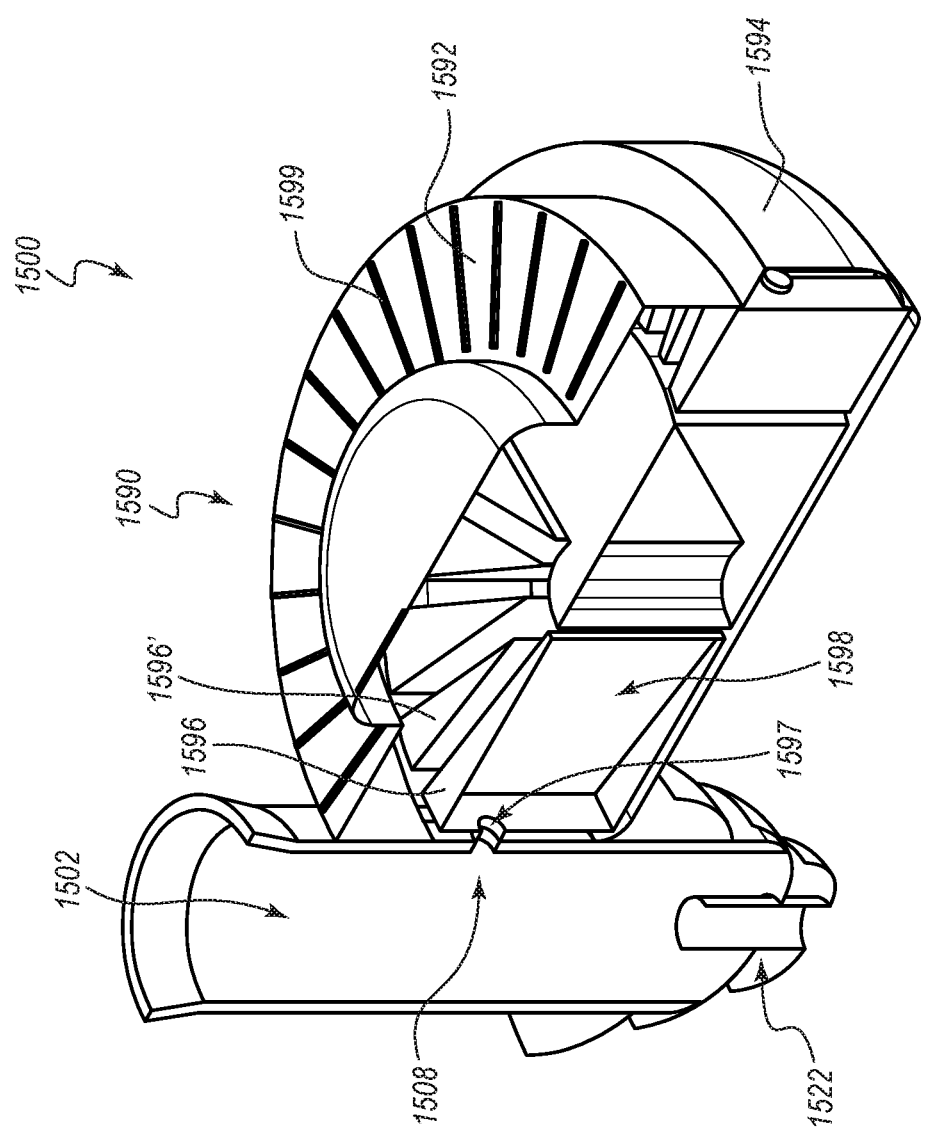
FIG. 29 is cross-sectional view of the sound-filtering device of FIG. 28.

FIGS. 28 and 29 depict another embodiment of a sound-filtering device 1500. In the illustrated embodiment, the sound-filtering device comprises an entry port 1502 and an insert portion 1522 comprising a resilient member 1540. The device 1500 further comprises an adjustable resonant chamber 1590. The adjustable resonant chamber 1590 comprises a rotational member 1592 that can be rotated within a housing 1594. The rotational member 1592 further comprises a plurality of discrete chambers 1596, 1596'.

Each discrete chamber 1596, 1596' can comprise a different fixed geometric volume 1598, and can correspond to a different attenuation or resonant frequency. The device 1500 can also be tuned by rotating the rotational member 1592 to a desired setting, which can be indicated by a dial 1591 comprising an indicia or marking. In some embodiments, the rotational member 1592 can further comprises markings 1599 that correspond with the discrete chambers 1596, 1596', which can also correspond to different attenuation settings. As the rotational member 1592 is rotated, the side port 1508 can align (or substantially align) with a port 1597 of a discrete chamber 1596, 1596', setting the resonant frequency.

FIG. 30 is a plot 1600 depicting illustrative examples of resonant frequency tuning profiles 1602, 1604 of an adjustable sound-filtering device, wherein the resonant frequency tuning profile 1602 with the higher frequency represents a profile generated by a device such as that depicted in FIG. 21, and the resonant frequency tuning profile 1604 with the lower frequency represents a profile generated by using an adjustment nozzle with the device, such as is depicted in FIG. 24. In FIG. 30, the resonant frequency for each profile was measured after each turn of the frequency adjustment member in reference to a flush position (a position in which the frequency adjustment member was flush with the proximal end of the resonant chamber).

As shown in FIG. 30, the resonant frequency can be adjusted by turning the frequency adjustment member to change its location within the resonant chamber. In particular, the target frequency (resonant frequency or frequency at which maximum attenuation is achieved) can be tuned by adjusting the geometric volume of the resonant chamber via turning the frequency adjustment member. As the frequency adjustment member is turned in one direction (e.g., in a direction towards the side port into the channel, or vice versa) the target frequency can be increased. Similarly, as the frequency adjustment member is turned in an opposite direction (e.g., in a direction away from the side port into the channel, or vice versa) the target frequency can be decreased. In some embodiments, instructions can be included that have such a plot depicting the relationship between turning the frequency adjustment member and the target frequency.

As further shown in FIG. 30, the target frequency can be further modified through use of an adjustment nozzle, such as is shown in FIG. 24. For example, an adjustment nozzle can be used to change the shape, size, and/or length of the neck or port from the resonant chamber into the channel. In some embodiments, such as the illustrated embodiment of FIG. 30, the frequency profile 1604 can be decreased through use of an adjustment nozzle as compared to the frequency profile 1602 obtained without use of an adjustment nozzle. In other embodiments, the frequency profile can be increased or otherwise modified as desired depending on the shape, size, and/or length of the adjustment nozzle.

Figure 31:
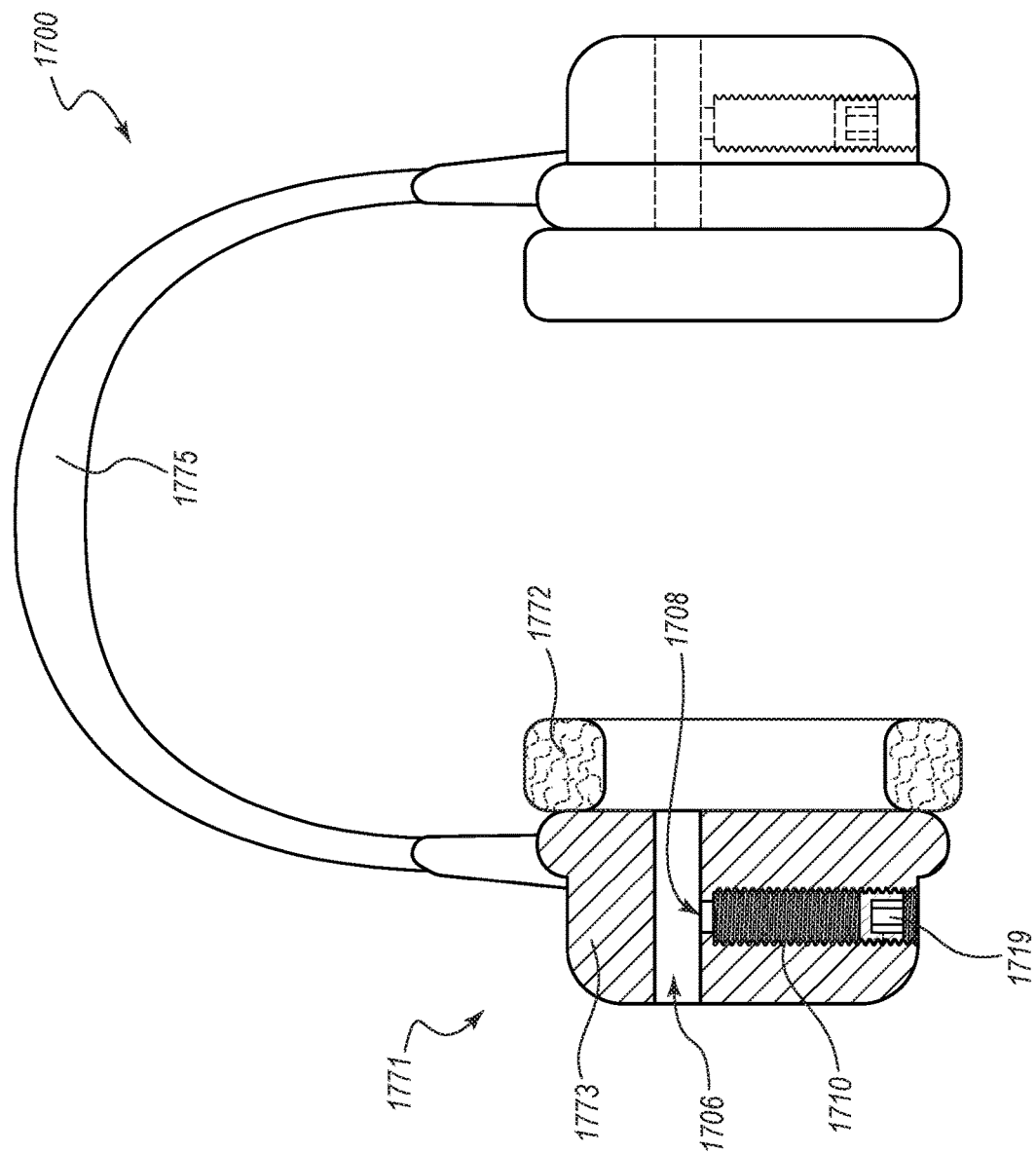
FIG. 31 depicts another embodiment of a sound-filtering device.

FIG. 31 depicts another embodiment of a sound-filtering device 1700. As shown in FIG. 31, in some embodiments, the sound-filtering device 1700 is incorporated into one or more headphones 1771. Various types and/or headphone 1771 configurations can be used. In some embodiments, the headphones 1771 can include a tether or headband 1775. The tether or headband 1775 can be used to couple two headphones 1771 together, and can be configured to wrap around a portion of the user's head. In other embodiments, only one headphone 1771 is used.

In certain embodiments, such as the illustrated embodiment, the headphone 1771 comprises a housing 1773 and pad 1772. When worn, the pad 1772 can be configured to abut a portion of the user's head. The pad 1772 can comprise a soft material. The pad 1772 can also be configured to be disposed over and/or around a user's ear. As can be appreciated, the headphone 1771, including the pad 1772, can be configured to cover the user's ear and inhibit and/or prevent sound from reaching the user's ear except via the channel 1706. In other embodiments, only a portion of the ear is covered by the headphone 1771.

As further shown in FIG. 31, the sound-filtering device 1770 includes a channel 1706 that extends through the housing 1773 of the headphone 1771. The channel 1706 also defines a path along which sound can travel from the environment to the user's ear. The sound-filtering device 1770 also includes a side port 1708 that extends from the channel 1706 to a resonant chamber 1710. The sound-filtering device 1770 also includes a frequency adjustment member 1719 that can be used to adjust the resonant frequency. It will be appreciated that various types of resonant chambers 1710 can be incorporated into the housing 1773 of the headphone 1771, as disclosed herein.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method illustrated in the drawings, such as a small subset of a step, may be a separate method. Stated otherwise, some additional methods may include only a portion of the steps shown in a more detailed method.

References to approximations are made throughout this specification, such as by use of the terms "substantially," "about" or "approximately." For each such reference, it is to be understood that, in some embodiments, the value, feature, or characteristic may be specified without approximation. For example, where qualifiers such as "substantially,"

"about" or "approximately" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows.

The invention claimed is:

1. A sound-filtering device comprising:
    an entry port configured to be exposed to an environment to receive sound from the environment when the device is coupled to a portion of an ear of a user;
    an exit port configured to deliver sound that has passed through the device to an ear canal of the user when the device is coupled to the portion of the ear of the user;
    a channel extending between the entry port and the exit port to define a path along which sound travels from the entry port to the exit port;
    a side port in fluid communication with the channel; and
    a resonant chamber offset from the path defined by the channel and in fluid communication with the channel via the side port, the resonant chamber being configured to attenuate at least a portion of any sound passing through the channel that is within a band of frequencies narrower than a full audible spectrum of the user, wherein a geometric volume of the resonant chamber is selectively adjustable, and wherein the resonant chamber is disposed outside the ear canal of the user when the device is coupled to the portion of the ear of the user.

2. The sound-filtering device of claim 1, wherein the resonant chamber is directed downwards relative to the channel when the device is coupled to the portion of the ear of the user.

3. The sound-filtering device of claim 1, further comprising:
    a housing element that defines a portion of the resonant chamber; and
    a frequency adjustment member having an end wall that defines a further portion of the resonant chamber and is selectively movable relative to the housing element to adjust the geometric volume of the resonant chamber and alter the band of frequencies within which at least a portion of any sound passing through the channel is attenuated.

4. The sound-filtering device claim 3, wherein the housing element defines an internal adjustment interface and the frequency adjustment member defines an external adjustment interface that cooperates with the internal adjustment interface to effect adjustment of the geometric volume of the resonant chamber.

5. The sound-filtering device of claim 3, wherein a reduction of the geometric volume corresponds to an upward shift of the band of frequencies within which at least a portion of any sound passing through the channel is attenuated.

6. The sound-filtering device of claim 3, wherein an increase of the geometric volume corresponds to a downward shift of the band of frequencies within which at least a portion of any sound passing through the channel is attenuated.

7. The sound-filtering device of claim 1, further comprising a first housing element that defines at least a portion of the channel and a second housing element defines at least a portion of the resonant chamber, wherein the second housing element is selectively attachable to and detachable from the first housing element.

8. The sound-filtering device of claim 7, wherein the first housing element defines the side port, and wherein the second housing element is configured to encompass the side port when attached to the first housing element.

9. The sound-filtering device of claim 1, further comprising a plurality of markings that represent different bands of frequencies within which at least a portion of any sound passing through the channel is attenuated.

10. The sound-filtering device of claim 9, wherein each marking corresponds to a frequency at which maximum attenuation is achieved.

11. The sound-filtering device of claim 1, wherein:
    the resonant chamber defines the geometric volume;
    wherein when the geometric volume is filled with air, the air resonates at a natural frequency; and
    the natural frequency is within the narrow band of frequencies.

12. The sound-filtering device of claim 1, further comprising an anchor system configured to couple the device to the portion of the ear of the user.

13. The sound-filtering device of claim 1, wherein the band of frequencies spans no more than two octaves.

14. The sound-filtering device of claim 1, wherein the device amplifies sound passing through the channel at frequencies adjacent to a lower end of the band of frequencies and at frequencies adjacent to an upper end of the band of frequencies.

15. The sound-filtering device of claim 1, wherein a minimum cross-sectional area of the channel in a direction transverse to a direction of travel of sound through the channel is no less than one third of an area defined by an outer perimeter of the device at a longitudinal position of the exit port.

16. The sound-filtering device of claim 1, wherein the device is free of electrical components.

17. A kit for alleviating the symptoms of tinnitus, the kit comprising:
   a sound-filtering device comprising:
      a channel extending between an entry port and an exit port to define a path along which sound travels through the device when the device is coupled to a portion of an ear of a user; and
      a resonant chamber offset from the path defined by the channel and in fluid communication with the channel via a side port, the resonant chamber being configured to attenuate at least a portion of any sound passing through the channel that is within a band of frequencies narrower than a full audible spectrum of the user, wherein a geometric volume of the resonant chamber is adjustable to alter the band of frequencies, and wherein the resonant chamber is disposed outside an ear canal of the user when the device is coupled to the portion of the ear of the user; and
   one or more of instructions for using the sound-filtering device or directions for accessing instructions for using the sound-filtering device, said instructions comprising directions to adjust the geometric volume to ensure that a frequency at which the user experiences tinnitus is within the band of frequencies within which at least a portion of any sound passing through the channel is attenuated.

18. The kit of claim 17, wherein the sound-filtering device further comprises:
   an end wall that delimits the geometric volume of the resonant chamber; wherein said instructions further comprise directions to:
   move the end wall to adjust the geometric volume of the resonant chamber.

19. A method of modifying sound for delivery to an eardrum of a user, the method comprising:
   obtaining a sound-filtering device comprising a resonant chamber that defines a first geometric volume, the resonant chamber being configured to attenuate at least a portion of any sound passing through the device that is within a first band of frequencies that is narrower than a full audible spectrum of the user when defining the first geometric volume;
   adjusting a size of the resonant chamber such that the resonant chamber defines a second geometric volume, the resonant chamber being configured to attenuate at least a portion of any sound passing through the device that is within a second band of frequencies that is narrower than the full audible spectrum of the user when defining the second geometric volume, wherein the second band of frequencies is different from the first band of frequencies; and
   coupling the sound-filtering device to a portion of an ear of the user such that the resonant chamber is disposed outside an ear canal of the user when the device is coupled to the portion of the ear of the user.

20. The method of claim 19, further comprising attenuating at least a portion of sound passing through the device via the resonant chamber after said coupling of the sound-filtering device to the portion of the ear of the user.

* * * * *